(12) United States Patent
Kamiyama et al.

(10) Patent No.: US 6,872,179 B2
(45) Date of Patent: Mar. 29, 2005

(54) MEDICAL DIAGNOSIS SYSTEM HAVING A MEDICAL DIAGNOSIS APPARATUS AND A DISPLAY TO BE OBSERVED BY A PATIENT

(75) Inventors: Naohisa Kamiyama, Tochigi-ken (JP); Akihiro Sano, Tochigi-ken (JP); Yoichi Ogasawara, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 138 days.

(21) Appl. No.: 10/191,476

(22) Filed: Jul. 10, 2002

(65) Prior Publication Data

US 2003/0026464 A1 Feb. 6, 2003

(30) Foreign Application Priority Data

Jul. 10, 2001 (JP) .................................... 2001-208720

(51) Int. Cl.[7] ............................................. A61B 8/00
(52) U.S. Cl. ....................................... 600/437; 600/443
(58) Field of Search ................................. 600/407–472; 73/625, 626; 367/7, 11, 130, 138; 128/916; 382/128; 700/231, 237; 705/2–3, 52, 56

(56) References Cited

U.S. PATENT DOCUMENTS

| 5,412,419 | A | | 5/1995 | Ziarati |
| 6,063,030 | A | * | 5/2000 | Vara et al. ................... 600/437 |
| 6,117,079 | A | * | 9/2000 | Brackett et al. ............. 600/437 |
| 6,526,163 | B1 | * | 2/2003 | Halmann et al. ........... 382/128 |
| 6,595,924 | B2 | * | 7/2003 | Kawae et al. ............... 600/437 |

FOREIGN PATENT DOCUMENTS

| JP | 1-249044 | 10/1989 |
| JP | 3141419 | 12/2000 |
| JP | 2001-137237 | 5/2001 |

* cited by examiner

Primary Examiner—Ali Imam
(74) Attorney, Agent, or Firm—Oblon, Spivak, McClelland, Maier & Neustadt, P.C.

(57) ABSTRACT

A medical diagnosis system wherein a medical image is produced in a medical diagnosis apparatus, comprises a first storage device which stores an examination procedure for the medical diagnosis apparatus, a second storage device which stores supply information, a supply device which supplies the supply information stored in the second storage device, and a control processor which controls that the supply information is supplied in the supply device in accordance with the examination procedure stored in the first storage device.

26 Claims, 10 Drawing Sheets

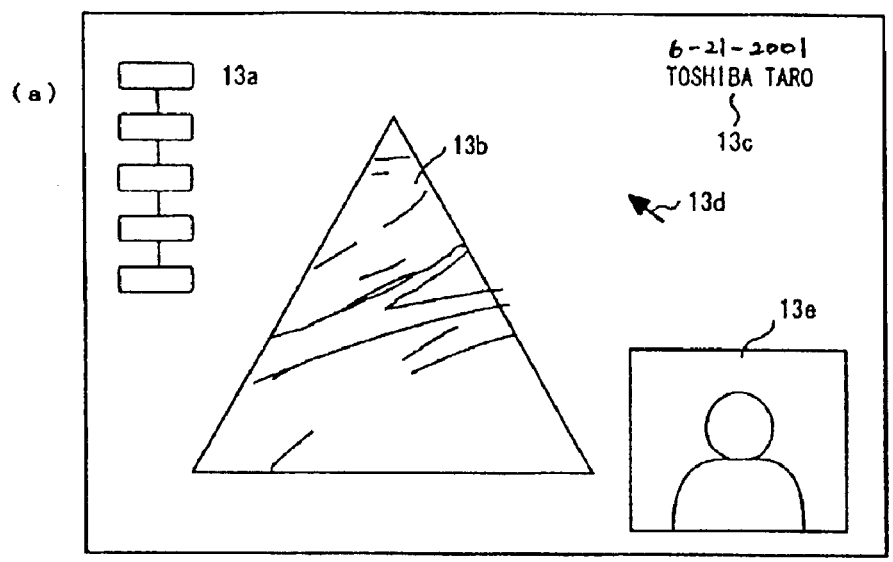
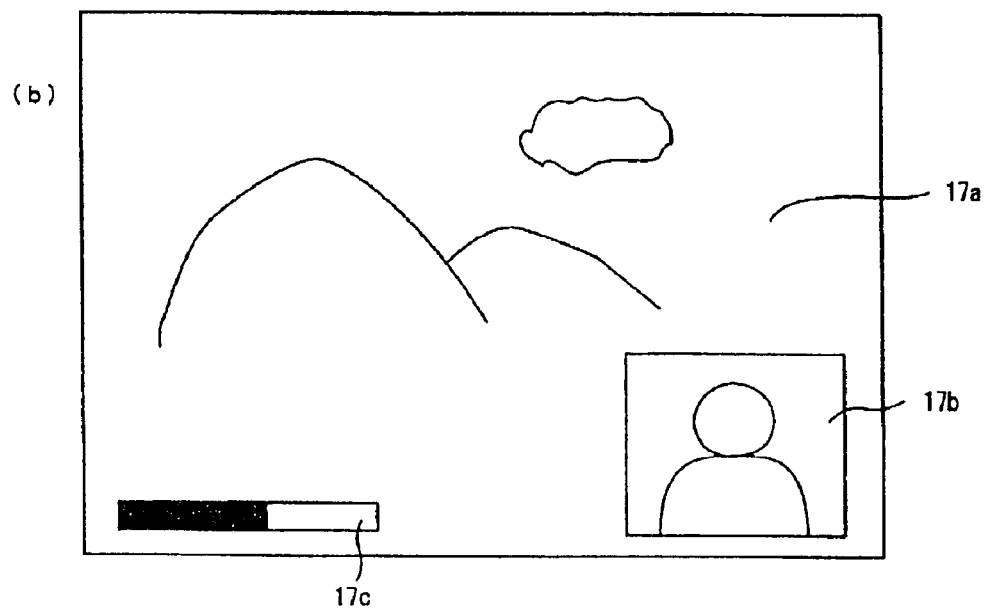
FIG. 2

| Exam. Name | Workflow Data | Contents (Actual Exam) | Supply Information |
|---|---|---|---|
| Myocardial Infarction Examination | Workflow Data A | • Basic US Diagnosis<br>• Heart Contrast Echo<br>• Reporting | • US Exam. Explanation<br>• Contrast Echo Exam. Explanation |
| Hepatic Cancer Examination | Workflow Data B | • Basic US Diagnosis<br>• Liver Contrast Echo<br>• Reporting | • US Exam. Explanation<br>• Contrast Echo Exam. Explanation |
| Fetal Growth Examination | Workflow Data C | • Basic US Diagnosis<br>• Fetus Measurement<br>• Reporting | • US Exam. Explanation<br>• Fetal Growth Explanation |

FIG. 4

MEDICAL DIAGNOSIS SYSTEM HAVING A MEDICAL DIAGNOSIS APPARATUS AND A DISPLAY TO BE OBSERVED BY A PATIENT

CROSS-REFERENCE TO RELATED APPLICATION

This application is based upon and claims the benefit of priority from prior Japanese Patent Application No. P2001-208720, filed on Jul. 10, 2001, the entire content of which is incorporated herein by reference.

FIELD OF THE INVENTION

The present invention relates to a medical diagnosis system including an apparatus for medical diagnosis by, for example, ultrasound, X-ray, X-ray computed tomography (hereinafter referred to as CT), or magnetic resonance imaging (hereinafter referred to as MRI), and displays to be observed by a patient and a person to be examined by the apparatus (hereinafter referred to as a patient), and to a method of controlling the medical diagnosis system. The present invention further relates to such an apparatus for medical diagnosis and to a display to be observed by a patient both of which are used in the medical diagnosis system.

BACKGROUND OF THE INVENTION

It has been known that a medical diagnosis apparatus provides reconstructed images which have high resolutions and objectivity for a use of medical diagnosis. The apparatus obtains the reconstructed images by receiving signals generated/reflected in a patient or signals transmitted through inside the patient and reconstructing the received signals. Concretely, such an apparatus is known as a CT apparatus, an MRI apparatus, an X-ray diagnosis apparatus, and an ultrasound diagnosis apparatus. These apparatuses make it possible to obtain image information with morphology, dynamic state, functionality, and the like of inside the patient.

A patient is usually placed under constraint for a certain time due to acquiring necessary diagnostic information in diagnosis by an apparatus. This patient-binding time may be dozens of minutes or sometimes over one hour, which depends on a kind of diagnosis examination by the apparatus. When a patient is examined by the apparatus, the patient is likely to be suffered from anxiety and boredom such as follows: "when the examination will be completed"; "what the purpose of rubbing sonic gel is in ultrasound diagnosis"; "what the purpose of attaching electrocardiographic equipment is"; "noise caused during the examination"; "placement into a narrow space of a CT apparatus or an MRI apparatus."

One of solutions to reduce the patient's suffering resulted from the examination, particularly run for a long time, is described in the Japanese Patent Application Disclosure No. 1-249044. This document discloses an MRI apparatus which enables a patient to watch TV or to see an MRI operator through a monitor during an examination.

Further, an operator of a medical diagnosis apparatus has been recently required more advanced skills and experiences of operations since such an apparatus has been recently highly sophisticated and medical diagnostic techniques have been more complicated. Accordingly, the examination performance depends on operators' skills and experiences. This could make examination results less reliable. One solution may be an introduction of a use of a workflow of examination procedures. Japanese Patent Application Disclosure No. 2001-137237 discloses an ultrasound diagnosis apparatus which switches its operation in accordance with a predetermined workflow examination procedures.

The above-mentioned Japanese Patent Application Disclosure No. 1-249044 is an example of reducing patient's suffering and boredom by supplying the patient with TV or video watching. Since, however, this entertainment is provided independently of the examination's progress, the patient can neither be explained nor directed of the examination at the appropriate timing.

An examination with an MRI apparatus usually is dependent on the apparatus itself and is completed according to a rule usually without any exception. Therefore, the examination time tends to be within a time frame expected before the examination. For example, once an operator tells a patient about an approximate time required for an MRI examination in advance, providing video watching is enough to reduce the patient's anxiety and fear of a confined space/a dark place, as described in the Disclosure. This is because there is not in particular much necessity of various directions and flexible responses according to the examination progress.

When it comes to an examination with, for example, an ultrasound diagnosis apparatus, the examination is highly dependent on skills and experiences of an operator. In the ultrasound diagnosis apparatus, the examination must be progressed flexibly according to necessity under the circumstance at a certain stage of the examination. This means that the followings may be required: the original examination may be interrupted and a new examination may be cut into the original examination; and unscheduled sub-examinations related to the original examination may be decided to be performed during the original examination, and after the unscheduled sub-examinations, the scheduled examination is resumed. Consequently, the examination's time and contents become different from the original ones.

Therefore, the patient has anxiety of when the examination will be finished, what will be done next, and so on. This is different from the MRI case in which the patient feels anxiety and fear from a confined space and noise due to a figure feature of an MRI apparatus.

On the other hand, from an operator's point of view, when the operator operates an ultrasound diagnosis apparatus, as mentioned before, the operator is required highly-trained skills and experiences so as to correctly follow complicated examination procedures and perform the examination.

As to this subject, the above-mentioned Japanese Patent Application Disclosure 2001-137237 introduces the operation changes in accordance with a workflow. However, although such a workflow is useful for the operator, this Disclosure still does not disclose any information supply to a patient.

Turning to various medical diagnosis apparatuses, a patient is usually required to change his or her body position and stop his or her breathing, following operator's directions during an examination. These directions are made in the operator's speech. Such directions in speech are not always sufficient to make the operator understood. Further, there is another problem of increase of operator's work by which the operator cannot concentrate on the examination itself. In an examination with a CT apparatus or an MRI apparatus, an operator operates the apparatus in other room from a patient and so it is quite difficult for the operator to direct or explain to the patient well.

BRIEF SUMMARY OF THE INVENTION

According to a first aspect of the present invention, there is provided a medical diagnosis system wherein a medical image is produced in a medical diagnosis apparatus, which comprises first storing means for storing an examination procedure for the medical diagnosis apparatus, second storing means for storing supply information, supply means for supplying the supply information stored in the second storing means, and controlling means for controlling that the supply information is supplied in the supply means in accordance with the examination procedure stored in the first storing means.

According to a second aspect of the present invention, there is provided a medical diagnosis system wherein a medical image is produced in a medical diagnosis apparatus, which comprises first storing means for storing a plurality of workflows each of which includes a corresponding examination procedure for the medical diagnosis apparatus, second storing means for storing a plurality of supply information, supply means for supplying the supply information stored in the second storing means, selecting means for selecting a workflow from the workflows stored in the first storing means, and controlling means for controlling that one of the supply information is supplied by the supply means in accordance with the workflow selected by the selecting means.

According to a third aspect of the present invention, there is provided a medical diagnosis system wherein a medical image is produced in a medical diagnosis apparatus, which comprises input means for input operations, storing means for storing supply information, supply means for supplying the supply information stored in the storing means, and controlling means for controlling that the supply information is supplied in the supply means in accordance with the input operations by the input means.

According to a fourth aspect of the present invention, there is provided a medical diagnosis system wherein a medical image is produced in a medical diagnosis apparatus, which comprises input means for inputting information regarding a patient, storing means for storing supply information, and supply means for supplying the supply information stored in the storing means on the basis of the information input by the input means.

According to a fifth aspect of the present invention, there is provided an ultrasound diagnosis apparatus for a use in a medical diagnosis system, which comprises image producing means for producing an ultrasound image, display means for displaying the ultrasound image produced by the image producing means, first storing means for storing an examination procedure related to the ultrasound diagnosis apparatus, second storing means for storing supply information, and controlling means for controlling that the supply information is output to an independent apparatus so as to be supplied to the independent apparatus in accordance with the examination procedure stored in the storing means.

According to a sixth aspect of the present invention, there is provided a medical diagnosis apparatus producing a medical image, which comprises a memory which stores an examination procedure related to the medical diagnosis apparatus, a second memory which stores supply information, and a processor which is operative to output the supply information to an independent apparatus so that the supply information is supplied to the independent apparatus in accordance with the examination procedure stored in the memory.

According to a seventh aspect of the present invention, there is provided an information apparatus for a use in a medical diagnosis system including a medical diagnosis apparatus which produces a medical image, which comprises first storing means for storing an examination procedure of the medical diagnosis apparatus, second storing means for storing supply information, supply means for supplying the supply information stored in the second storing means, and controlling means for controlling that the supply information is supplied in the supply means in accordance with the examination procedure stored in the first storing means.

According to an eighth aspect of the present invention, there is provided an information apparatus for a use in a medical diagnosis system including a medical diagnosis apparatus which produces a medical image, which comprises receiving means for receiving an information signal output from the medical diagnosis apparatus, storing means for storing supply information, supply means for supplying the supply information stored in the storing means, and controlling means for controlling that the supply information is supplied in the supply means in accordance with the information signal received by the receiving means.

According to a ninth aspect of the present invention, there is provided a method of controlling a medical diagnosis system wherein a medical image is produced in a medical diagnosis apparatus, which comprises steps of selecting an examination procedure, operating the medical diagnosis apparatus in accordance with the selected examination procedure, and switching one piece of supply information to another piece of supply information in accordance with the selected examination procedure, the supply information being supplied to a patient.

According to a tenth aspect of the present invention, there is provided a method of controlling a medical diagnosis system wherein a medical image is produced in a medical diagnosis apparatus, which comprises steps of selecting a plurality of examination procedures, operating the medical diagnosis apparatus in accordance with the selected examination procedures, and supplying a patient with supply information corresponding to each kind of the selected examination procedures.

According to a eleventh aspect of the present invention, there is provided a method of controlling a medical diagnosis system wherein a medical image is produced in a medical diagnosis apparatus, which comprises steps of selecting one examination from a plurality of examinations, displaying a plurality of examination procedures corresponding to the one selected examination, selecting each examination procedure from the displayed examination procedures, and supplying a patient with supply information corresponding to the each selected examination procedure.

According to a twelfth aspect of the present invention, there is provided a computer-readable medium on which is stored a program module for supplying a patient with information in a medical diagnosis system wherein a medical image is produced, the program module comprising instructions, which when executed perform steps comprising selecting one examination from a plurality of examinations, displaying a plurality of examination procedures corresponding to the one selected examination, selecting each examination procedure from the displayed examination procedures, and supplying the patient with supply information corresponding to the each selected examination procedure.

BRIEF DESCRIPTION OF THE DRAWINGS

A more complete appreciation of embodiments of the present invention and many of its attendant advantages will be readily obtained by reference to the following detailed description considered in connection with the accompanying drawings, in which:

FIG. 4 is a table showing a relation among a examination name, workflow data, contents of the examination, and supply information;

DETAILED DESCRIPTION OF THE PREFERRED EMBODIMENTS

Embodiments of the present invention will be described with reference to the accompanying drawings.

(First Embodiment)

Figure 1:
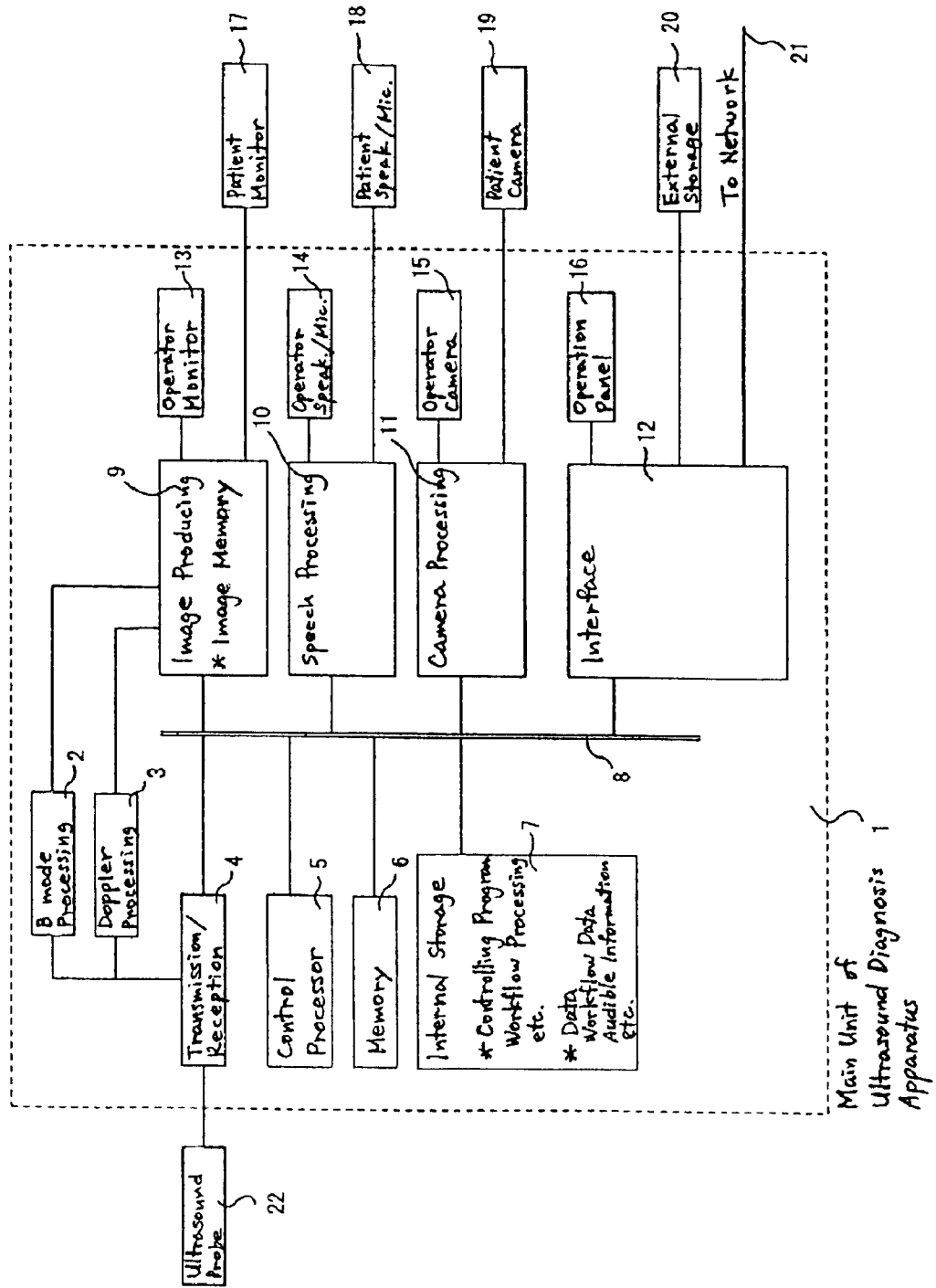
FIG. 1 is a block diagram showing an ultrasound diagnosis system according to a first embodiment of the present invention.

FIG. 1 is a block diagram showing an example ultrasound diagnosis system according to a first embodiment of the present invention. The ultrasound diagnosis apparatus comprises a main unit 1 and an ultrasound probe 22.

The main unit 1 of the ultrasound diagnosis apparatus comprises a B mode processing circuitry 2, a Doppler processing circuitry 3, a transmission/reception circuitry 4, a control processor 5, a memory 6, an internal storage device 7, bus 8, an image producing circuitry 9, a speech processing circuitry 10, a camera processing circuitry 11, an interface circuitry 12, an operator monitor 13, an operator speaker/microphone 14, an operator camera 15, and an operation panel 16.

The ultrasound probe 22 has an array of ultrasound vibration elements for converting between ultrasound signals and electric signals. The ultrasound probe 22 transmits and receives ultrasound signals to/from a patient. The transmission/reception circuitry 4 comprises a transmission circuit and a reception circuit. The transmission circuit generates driving signals for making the array of ultrasound vibration elements transmit ultrasound signals. The reception circuit performs delayed addition processing on ultrasound echo signals received from each ultrasound vibration element and generates ultrasound echo signals corresponding to a predetermined scanning raster.

The B mode processing circuitry 2 performs processing, such as logarithmic transformation, and envelope detection on ultrasound echo signals. B mode images are produced on the basis of output signals of the B mode processing circuitry 2. The B mode images are density-distributed images, in two dimensions, where the signal strength of ultrasound echo signals visibly appear in the images as the tissue structure inside a patient's body and the enhancing agent.

The Doppler processing circuitry 3 performs processing of such as orthogonal detection, MTI (moving target indicator) filtering, and auto correlation, to the ultrasound echo signals. As a result, speed values, dispersion values, and power values, of moving bodies inside the patient's body can be obtained. CFM (color flow mapping) images produced on the basis of output signals of the Doppler processing circuitry 3 are images obtained by assigning colors, in accordance with a certain rule, to the speed values, the dispersion values, and the power values. This makes it possible to observe speed, dispersion, and power of moving bodies such as the blood flow, the enhancing agent, and the body tissue.

The internal storage device 7 is implemented as a mass magnetic storage means which is randomly accessible like HDD (hard disk drive). The internal storage device 7 digitally stores speech data, image data, workflow data for examination procedures, and a control program for controlling the ultrasound diagnosis apparatus and implementing a workflow-processing. The workflow data is information of sequences of operation control items (hereinafter referred to as activities) defining operations of the ultrasound diagnosis apparatus.

Each activity has a name of its activity, icon information, and an operation (or an action) of the ultrasound diagnosis apparatus. Further, each activity is given a definition of (a) scanning mode switching among the B mode, the CFM mode, and the enhancing mode, (b) change of transmission/reception condition of the ultrasound diagnosis apparatus, (c) start/termination of a measurement program for ultrasound diagnosis, (d) message display to an operator, (e) change or switching of supply information (herein "change" may include modifying one supply information in which at least a part of the one supply information is remained in the modified supply information and "switching" may include replacing one supply information with another. In this specification and attached claims, however, when a word "switching" or the like in an appropriate form as required in each sentence is used for supply information, such word may include the meaning(s) of either or both of the "change" and the "switching" as appropriately.) (herein "supply information" may be information to be supplied to a patient during an examination, such as, for example, an examination explanation, a direction to a patient, a message to a patient, an animation, a music, a song, an image which makes a patient feel comfortable or relaxed mentally, a medical diagnosis image, an image of an operator, a moving picture, a TV program, and so on, in a visible form and/or in an audible form.), and so on. Contents of activities may be pre-determined and stored at the time of delivery of the apparatus, or may be determined and set by an operator on his or her own.

The workflow-processing program sequentially executes each activity based on the workflow data. Accordingly an operation or an action of an apparatus is switched and operation directions are given to an operator. Further, the internal storage device 7 may also store data of ultrasound diagnosis images acquired during an examination.

The control processor 5 controls each circuitry or part of inside the apparatus based on the control program stored in the internal storage device 7. In this embodiment, the memory 6 is constituted of a high-speed semiconductor memory such as a RAM (random access memory). When the control processor 5 controls as mentioned above, the memory 6 temporarily stores the control program, the workflow data, acquired ultrasound diagnosis images and so on.

The image producing circuitry 9 has an image memory for storing images. The image producing circuitry 9 produces, on the image memory, images to be displayed in the operator monitor 13 and images to be displayed in a patient monitor 17. The images on the image memory are output as video signals in a conventional video format. On this output occasion, if necessary, the image producing circuitry 9 writes data in a row along with each ultrasound scanning direction, the data being output from the B mode processing circuitry 2 and the Doppler processing circuitry 3, onto the image memory in correspondence with its scanned form. Then, the image producing circuitry 9 performs scan-conversion and produces ultrasound images.

The operator monitor 13 is configured with the main unit 1 of the ultrasound diagnosis apparatus and displays ultrasound images, activity icons, apparatus setting information, images and/or moving pictures taken by camera, and so on. The patient monitor 17 is configured in a manner possible to place in a position remote from the main unit 1 and is used in a position where a patient can see the patient monitor 17. The patient monitor 17 displays time information including time for the rest of the examination, image information which makes a patient feel comfortable or relaxed mentally, images and/or moving pictures taken by camera, and so on.

The speech processing circuitry 10 supplies driving signals to the operator speaker/microphone 14 and a patient speaker/microphone 18 so as to generate audible signals including speech information, music, or sound therefrom. Further, the speech processing circuitry 10 also converts audible signals collected through the operator speaker/microphone 14 and the patient speaker/microphone 18 into digital signals. The operator speaker/microphone 14 is configured with the main unit 1 of the ultrasound diagnosis apparatus, and supplies audible signals to and collects voice signals uttered by the operator. The patient speaker/microphone 18 is placed adjacent to the patient, and supplies audible signals to and collects voice signals uttered by the patient.

The camera processing circuitry 11 converts image and/or moving-picture signals taken by the operator camera 15 and the patient camera 19 into digital signals. The operator camera 15 is positioned to be able to take an operator's face or so. The patient camera 19 is positioned adjacent to a patient so as to be able to take a patient's face or so.

The interface circuitry 12 makes it possible to connect with among an external storage device 20, communication lines 21 to connect with a hospital's LAN (local area network), the operation panel 16, and other components in the main unit 1. The operation panel 16 has a keyboard, buttons for controlling the ultrasound diagnosis apparatus and for setting image quality conditions, and a pointing device such as a trackball and a mouse. The bus 8 transfers data to and from among each component in the ultrasound diagnosis apparatus.

Figure 2A:
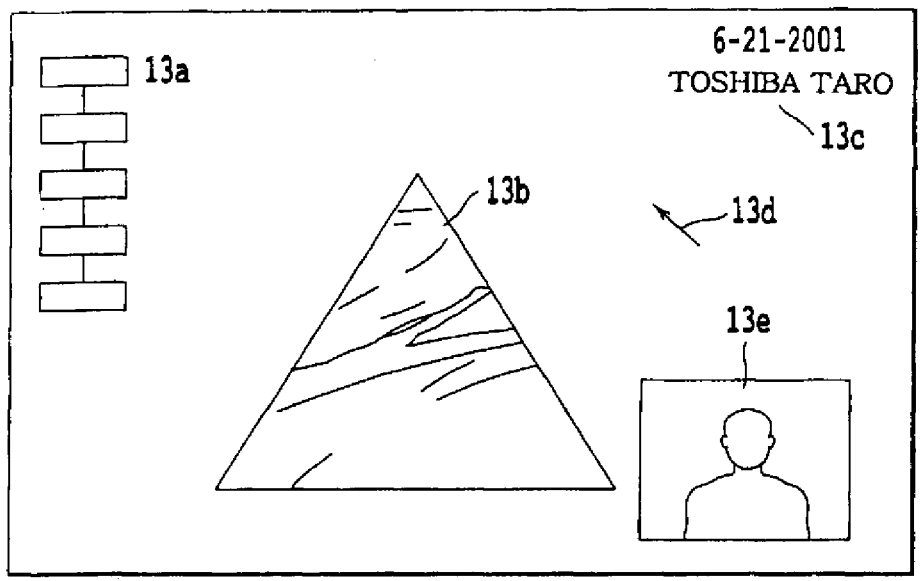
FIGS. 2(a) and 2(b) are examples showing display windows according to the first embodiment of the present invention.
Figure 2B:
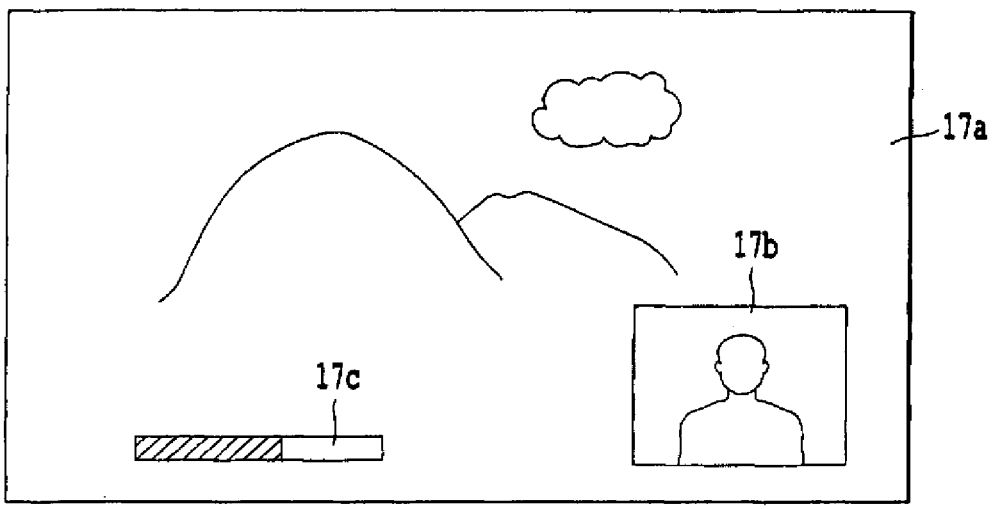
Figure 3:
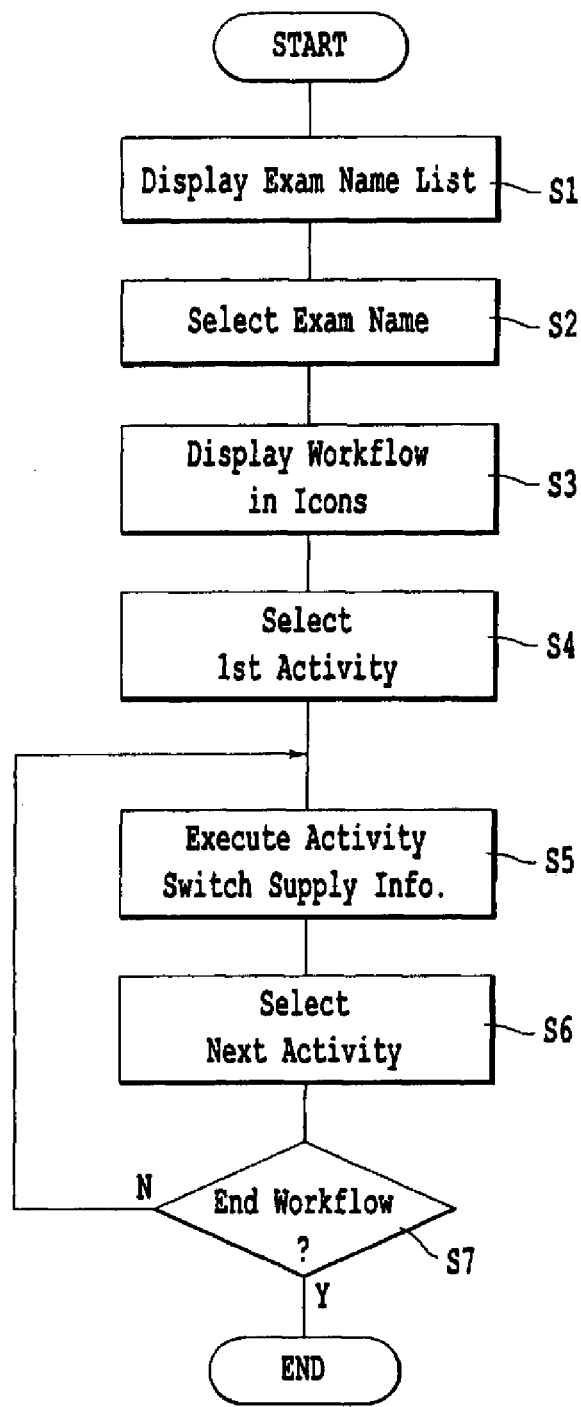
Figure 5:
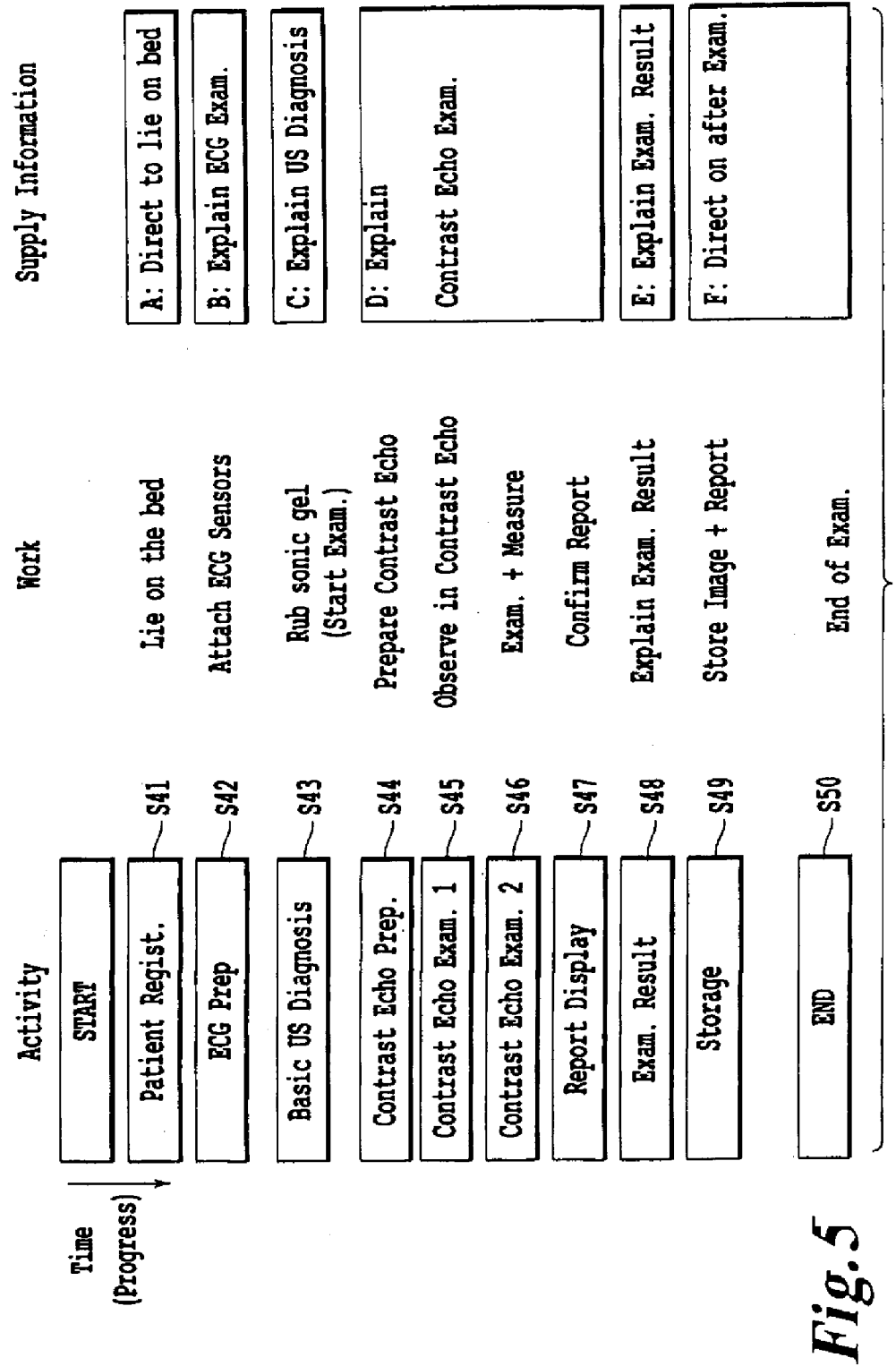

FIG. 2(*a*) is an example showing a display window of the operator monitor 13 according to the first embodiment of the present invention. The operator monitor 13 may display an icons' group 13*a* laid out one by one in a row each of which corresponds to an activity. The monitor 13 may also display an ultrasound image 13*b*, information 13*c* related with an examination (such as examination date), patient's information, etc, a cursor 13*d* moving in conjunction with operations to the pointing device on the operation panel 16, and a small display window 13*e* which displays an image or a moving picture taken by the patient camera 19. FIG. 2(*b*) is an example showing a display window of the patient monitor 17 according to the first embodiment of the present invention. The patient monitor 17 may mainly display a landscape image 17*a* which makes a patient feel comfortable or relaxed mentally over its display. In addition, the patient monitor 17 may also display a small display window 17*b* which displays an image or a moving picture taken by the operator camera 19, and a time progress bar 17*c* indicating time for the rest of an examination.

Figure 3:
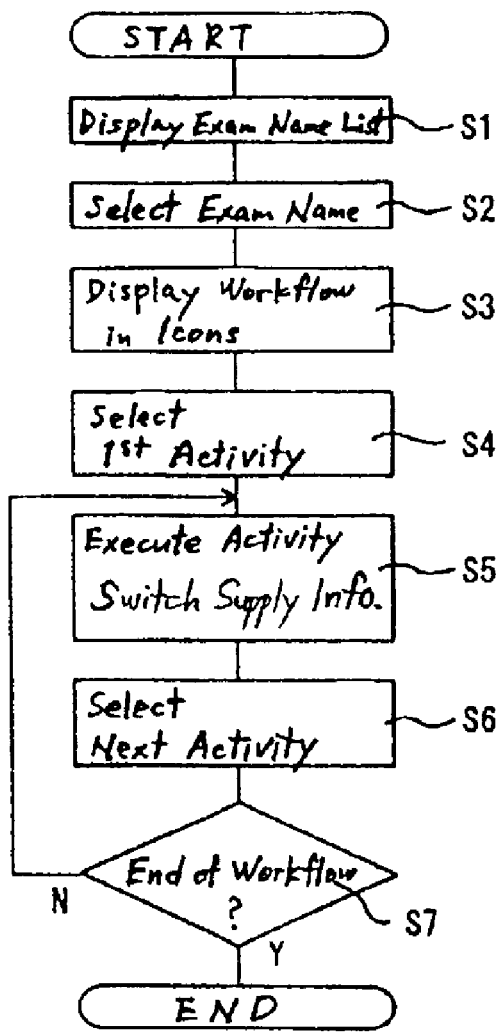
FIG. 3 is a flowchart showing a workflow-processing program according to the first embodiment of the present invention.

FIG. 3 is a flowchart showing a workflow-processing program according to the first embodiment of the present invention. When an operator presses an examination start button on the operation panel 16 of the ultrasound diagnosis apparatus, the workflow-processing program begins. First, the workflow-processing program makes a list of examination names each of which corresponds to each workflow data stored in the internal storage device 7, and then displays the list in the operator monitor 13 (step S1). Examples of examination names are a myocardial infarction examination, a hepatic cancer examination, and a fetal growth examination. As shown in a table of FIG. 4, each examination name is given workflow data, contents of the examination, and supply information which correspond thereto. The contents of the examination indicate several actual examinations to be performed by medical diagnosis apparatuses (hereinafter referred to as an actual examination). Therefore, an examination corresponding to a certain examination name may include several actual examinations. Responsive to a selected examination name, corresponding workflow data is implemented and corresponding supply information is displayed.

Next, the workflow-processing program waits for input so that an examination name can be selected from the list of examination names. Accordingly, an operator selects an examination name in operation with the operation panel 16 (step S2).

The workflow processing program reads out workflow data corresponding to the examination name selected in step S2, and controls the operator monitor 13 to display, in icons, activities, part of which corresponds to actual examinations, defined in the read out workflow data (step S3). A plurality of icons each of which corresponds to each activity are displayed in the order of execution in the operator monitor 13. Looking at the ordered icons, the operator may viscerally figure out a flow of the activities (actual examinations).

The workflow-processing program selects an activity to be executed first. The workflow processing program emphasizes an icon, in the operator monitor 13, corresponding to the selected activity in a color and/or a size different from the others (step S4).

Next, the workflow-processing program executes an operation or an action defined in the selected activity, and controls to change a setting of the ultrasound diagnosis apparatus and to display a message to the operator, in accordance with the defined operation or action. At this time, if any definition is included in the selected activity, regarding start and/or stop of supplying supply information, and/or switching of supply information, the contents of images or speech directions to be supplied to the patient may be switched in response to the definition (step S5). The internal storage device 7 may store in advance one or more kinds of moving pictures, animations, speech directions, messages, and the like as supply information. Each activity may be defined which of the above information to be supplied.

When execution of one activity is completed, the workflow processing program selects a next activity and emphasizes an icon, in the operator monitor 13, corresponding to the selected activity in a similar manner as explained before (step S6). If the selected activity is defined as 'end of workflow', this workflow processing is terminated. If the selected activity is not, the workflow processing goes back to the step S5 and executes the selected activity (step S7).

According to the above, each activity is normally executed in order. However, on the execution process of the ordered activities, the operator may alternatively select any icon, which is not necessary to be the next one, displayed in the operator monitor 13 by operating the mouse. In this case, an activity corresponding to the selected icon is going to be executed next. This means that an operation or an action is implemented according to the activity corresponding to the selected icon. The operation or the action includes supply of the appropriate supply information to the patient.

During the procedures following the flowchart shown in FIG. 3, the time progress bar 17c can be displayed in the patient monitor 17 so that the patient can recognize the time for the rest of the examination. The time progress bar 17c is configured from a frame showing an expected total time of the examination and a bar showing a progress of the examination. The bar is provided in the frame and changes its length according to the progress. The expected total time may be stored for each workflow data. Alternatively, a standard length of each actual examination is stored for each activity. A sum of the standard lengths corresponding to actual examinations included in the workflow data may be used as the expected total time. The progress time is calculated by correcting actual time elapsed in the actual examination, in conjunction with activity switching or the like. With such a time progress bar 17c displayed, the patient can recognize to what extent the examination is progressing and/or how long it takes until the examination will be finished.

The display of information related with the examination time is not limited to the above examples, but may be realized in any possible manner including conventional manners. For example, time information may be displayed in a chart form or in characters only. Further, displayed information may be only an expected total time, only an elapsed time, or a combination of those in any form. Additionally, those skilled in the art will appreciate that display to the patient is not limited to a visual display, but may be speech display through the patient speaker/microphone 18.

When the operator operates the operation panel 16 and directs to display an image or a moving picture taken by camera, an image or a moving picture of the operator taken by the operator camera 15 is displayed in the small display window 17b of the patient monitor 17. An image or a moving picture of the patient taken by the patient camera 19 is displayed in the small display window 13e of the operator monitor 13. Also, the operator and the patient may communicate with each other through the operator speaker/microphone 14 and the patient speaker/microphone 18, and so they can see each other's facial expression as they talk.

Furthermore, it is another example to transmit, to a PC remote from an examination room via the communication lines 21, images or pictures taken by the operator camera 15 and the patient camera 19 and audible signals collected through the operator speaker/microphone 14 and the patient speaker/microphone 18. In a remote place with the PC, a doctor may be able to observe the examination case and the patient condition on the PC. In this case, if there is provided in the remote place a doctor camera for taking the doctor and a doctor speaker/microphone for sending the doctor's voice and for hearing the operator and/or the patient, it may be possible to send the doctor's face or figure taken by the doctor camera via the communication lines 21 and display them in the operator monitor 13 and/or the patient monitor 17. In addition, the doctor's voice may be audible via the communication lines 21 through the operator speaker/microphone 14 and/or the patient speaker/microphone 18. Under this circumstance, the doctor may discuss a diagnosis with the operator while the doctor and operator are looking at each other. Furthermore, the doctor may also ask the patient about his or her condition while the doctor and patient are looking at each other.

Figure 5:
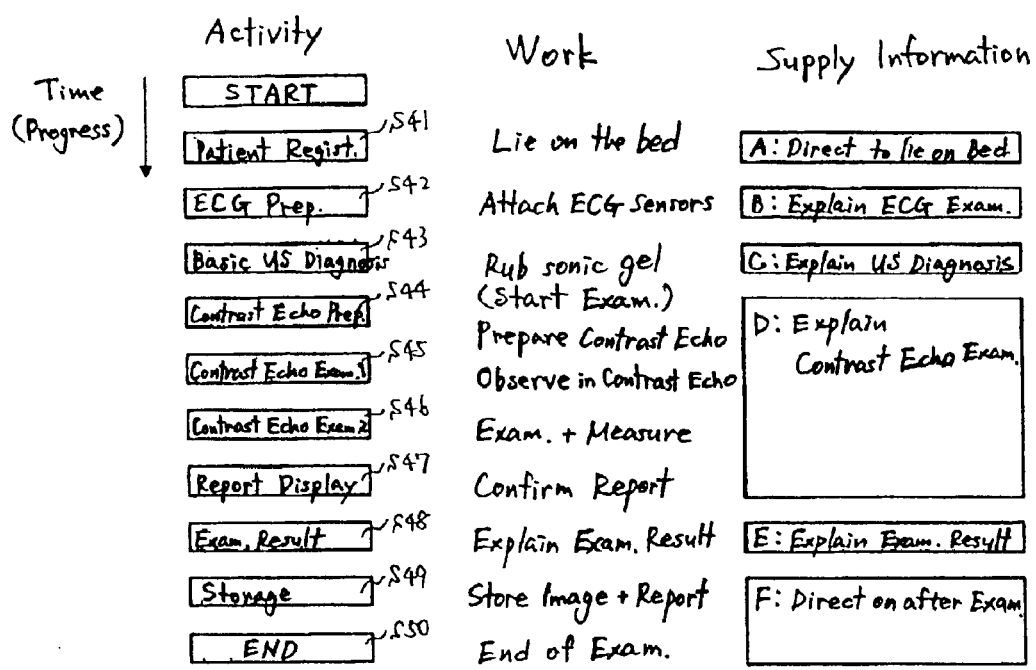
FIG. 5 is a schematic view showing relations between examinations and supply information following a workflow according to the first embodiment of the present invention.
Figure 6:
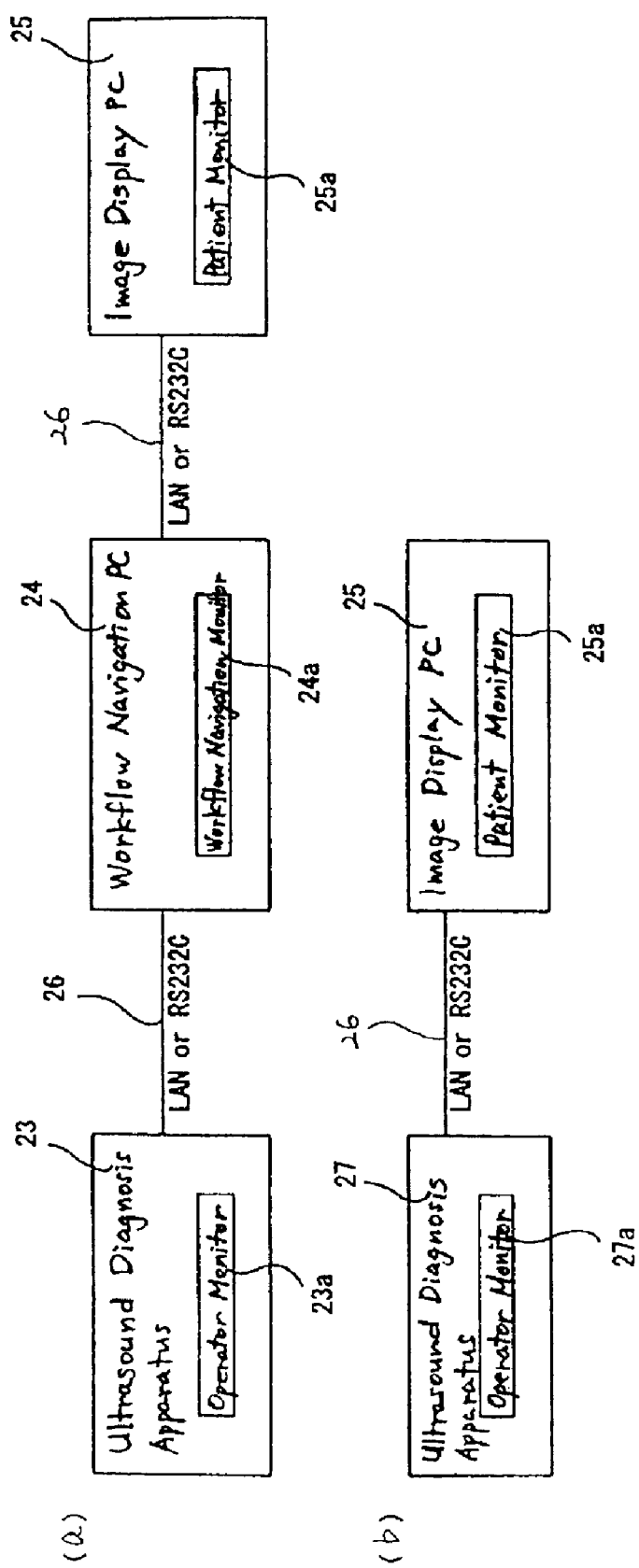
FIGS. 6(a) and 6(b) are block diagrams showing ultrasound diagnosis systems according to a second and a third embodiments of the present invention.

Next, FIG. 5 is a schematic view showing relations between examinations and supply information following a workflow according to the first embodiment of the present invention. In FIG. 5, activities included in a workflow are shown on the left side. Each operation of an operator or a patient corresponding to each activity is shown in the center. Further, supply information to the patient is shown on the right where a piece of the supply information corresponds to one or more activities.

Once the workflow processing program starts, a first activity "patient registration" (step S41) is executed. While the operator monitor 13 displays a window for registering patient information, the workflow-processing program controls the patient monitor 17 to display a direction-message, in characters, of 'please lie on the bed' with animation images (supply information A) which explains and shows how to lie on the bed for a coming examination. The patient lies on the bed, following this direction.

The operator may press a completion button after confirming that the patient has lain on the bed. The workflow-processing program, responsive to the button, executes a next activity "electrocardiographic equipment preparation" (step S42), and controls the operator monitor 13 to display a message to urge the operator to prepare an electrocardiographic equipment. During the urging, the workflow processing program controls the patient monitor 17 and the patient speaker/microphone 18 to supply an explanation of an actual examination by the equipment as supply information B. For example, the explanation may be supplied in forms of moving pictures, characters, animation images, and/or audible information. The explanation may also include the purpose of monitoring the electrocardiogram, diseases which may be diagnosed by the equipment, safety (for example, there is no worry that sensors to be attached to patient's skin are harmful), and so on. Accordingly, the patient wears sensors of the equipment.

The operator may press a completion button after completing the electrocardiographic equipment preparation. The workflow processing program, responsive to the button, executes a next activity "basic ultrasound diagnosis" (step S43), and controls the ultrasound diagnosis apparatus to change its mode (among B mode, CFM mode, and the like) and transmission/reception conditions. At the same time, the program also controls the operator monitor 13 to display a message to urge basic ultrasound diagnosis. Following the message, the operator rubs sonic gel onto the patient's body and observes ultrasound images around examination parts and their periphery.

During this observation, the workflow processing program controls the patient monitor 17 and the patient speaker/microphone 18 to supply an explanation of the ultrasound diagnosis as supply information C. For example, the explanation may be supplied in forms of moving pictures, characters, animation images, and/or audible information. The explanation may also include the purpose and contents of the ultrasound diagnosis, diseases which may be diagnosed by the ultrasound diagnosis, safety of the ultrasound diagnosis, and so on.

The operator may press a completion button after completing the basic ultrasound diagnosis. The workflow-processing program, responsive to the button, executes a next activity "contrast echo preparation" (step S44), and controls the operator monitor 13 to display a message to urge preparation for ultrasound contrast echo diagnosis. Following the message, the operator prepares for the ultrasound contrast echo diagnosis. At the same time, the workflow processing program controls the patient monitor 17 and the patient speaker/microphone 18 to supply an explanation of a contrast echo examination and relaxing information as supply information D. For example, the explanation may be supplied in forms of moving pictures, characters, animation images, and/or audible information. The explanation may include the purpose and contents of the ultrasound contrast echo diagnosis, diseases which may be diagnosed by the ultrasound contrast echo diagnosis, and the like. After the explanation has been supplied, there may also be supplied a landscape image which makes a patient feel comfortable or relaxed mentally, an image of a well-known picture, music, and/or the like. For children, it may also be suggested to supply an image, sound, and/or audible information such as a TV program, an animation image, and a song.

The operator may press a completion button after completing the contrast echo preparation. The workflow processing program, responsive to the button, executes a next activity "contrast echo examination 1" (step S45). Responsive to the operator's press of a completion button in turn, the workflow processing program executes an activity "contrast echo examination 2" (step S46) and an activity "report display" (step S47) in turn. Until the activity of the report display is completed, the supply information D as explained above continues to be supplied in the patient monitor 17 and the patient speaker/microphone 18. In the contrast echo examination 1, an observation is made regarding the ultrasound images in initial, medium, and late phases, respectively, after administering the enhancing agent. In the contrast echo examination 2, an actual examination is performed for obtaining quantification values of blood flow or the like from the ultrasound images with a measurement software executed. In the report display, the operator monitor 13 displays as a report a list of the obtained quantification values, comments of the operator, and so on. The operator confirms the displayed report.

The operator may press a completion button after confirming the displayed report. The workflow processing program, responsive to the button, executes a next activity "explanation of examination result" (step S48), and controls the operator monitor 13 to display an ultrasound image acquired in the examination and at the same time the patient monitor 17 to display the same image as supply information E. In this case, a cursor is displayed at the same position in both the operator monitor 13 and the patient monitor 17, respectively. The cursor moves in conjunction with operations of the mouse of the operation panel 16. The operator explains an examination result to the patient in speech, pointing out parts of the ultrasound image with the cursor.

Next, the operator may press a completion button after explaining the examination result. The workflow-processing program, responsive to the button, executes a next activity "storage" (step S49), and controls the internal storage device 7 to store the acquired ultrasound images and the report information as the examination result. Alternatively, instead of storing to the internal storage device 7, the ultrasound images and the report information may be stored in a data storage apparatus provided in a hospital by transmitting the images and the information via the communication lines 21 (a network).

During the storage, the workflow-processing program controls the patient monitor 17 and the patient speaker/microphone 18 to supply supply information F. For example, the supply information F may include directions to the patient about what to do after the examination has become over and a location map inside the hospital. The directions may also be about that the patient should go back to a ward, go to a pharmacy, or the like. The map may also help the patient to reach each directed place. The supply information F is typically supplied until the end of this workflow processing.

Responsive to the completion of the storage, the workflow-processing program executes a final activity "termination" (step S50). This workflow-processing program is terminated responsive to the press of a completion button.

According to the first embodiment of the present invention, supply information is switched in conjunction with kinds of activities (e.g., kinds of actual examinations) and progress of workflow processing. Accordingly, it is possible to supply the patient with the following exemplary supply information at the appropriate timing, respectively, during the examination: explanation of the actual examination, directions during the actual examination, information of the examination result, and information, such as images, moving pictures, music, and the like, which makes the patient feel comfortable and relaxed mentally. Such supply information makes it possible to reduce anxiety and/or boredom of the patient since, as explained above, the appropriate explanation is made to the patient regarding contents of the (actual) examination. Further, directions about the body positions such as a sitting position, a supine position, a lateral position, and the like are made appropriately and plainly so that the examination progresses preferably. As a result, the examination efficiency is improved.

In addition, the operator may perform a better-quality examination if the operator is allowed, any time when necessary, to direct a fine adjustment of the body position to the patient by cutting in the workflow in speech and/or a camera picture.

Further, since supply information is switched in accordance with kinds of activities data (e.g., kinds of actual examinations) and progress of workflow processing, the operator may be released from tangled and cumbersome operations for switching the supply information. This results in improvement of the examination efficiency.

Furthermore, supply information may be prepared and selected in accordance with the patient's age, sex, medical condition, etc. registered in the patient registration. If supply information has been prepared for the above case and is selected in accordance with the information of patient's age, sex, medical condition, etc., more appropriate supply information may be supplied to the patient.

Still further, examination time information is also supplied in the patient monitor 17 so that the patient can easily recognize, during the examination, to what extent the examination or each actual examination has been completed or how long it would take until the examination is completed. Accordingly, the patient's anxiety and boredom may be reduced.

(Second Embodiment)

The first embodiment was an example showing that the workflow processing and the production of image data and speech data for a patient were implemented in the main unit 1 of the ultrasound diagnosis apparatus. A second embodiment of the present invention is an example showing that the workflow processing and the production of image data and speech data for a patient is implemented in an independent personal computer (hereinafter referred to as PC).

Figure 6A:
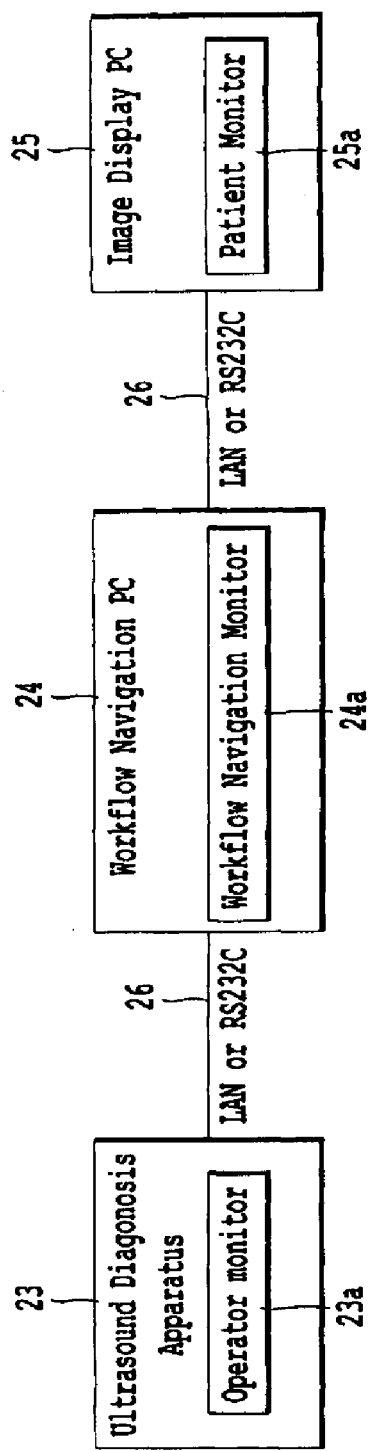

FIG. 6(a) is a block diagram showing an ultrasound diagnosis system according to the second embodiment of the present invention. In this embodiment, the same components as those described in the first embodiment are omitted to avoid potential confusion.

The ultrasound diagnosis system comprises an ultrasound diagnosis apparatus 23, a workflow navigation PC 24, and an image display PC 25. These components are connected to one another in a mutually communicable form via a hospital LAN or communication lines 26 such as RS232C. In addition, the ultrasound diagnosis apparatus 23 has an operator monitor 23a. The workflow navigation PC 24 has a workflow navigation monitor 24a. The image display PC 25 has a patient monitor 25a.

In this embodiment, each of the workflow navigation PC 24 and the image display PC 25 is constituted from a conventional PC which is commercially available and includes a CPU (central processing unit), a memory, a magnetic storage device, a bus, and input means such as a keyboard and a mouse. In the workflow navigation PC 24, a workflow processing program and a workflow data are stored in the magnetic storage device. In the image display PC 25, an image display program and supply information, such as image data and speech data, are stored in the magnetic storage device.

The workflow-processing program is executed in the workflow navigation PC 24 and performs operations in a similar manner as described in the first embodiment of the present invention. The workflow processing program controls the workflow navigation monitor 24a to display a list of examination names, icons corresponding to activities, and the like. The workflow-processing program also executes each activity sequentially and transmits control signals to the ultrasound diagnosis apparatus 23 and the image display PC 25 via the communication lines 26. The control signals are produced in accordance with the contents defined in each activity. Responsive to the control signals, the ultrasound diagnosis apparatus 23 changes its setting and operations, and the image display PC 25 switches when to supply the supply information and switches supply information at the appropriate times. Switching supply information corresponding to one activity to supply information corresponding to the next activity may be responsive to an input with a keyboard or a mouse of the workflow navigation PC 24. Alternatively, such switching may be implemented by transmitting, to the workflow navigation PC 24 via the communication lines 26, information of a current operation status of the ultrasound diagnosis apparatus 23 or information input to the operation panel 16.

According to the second embodiment of the present invention as described above, supply information is switched in conjunction with the progress of the examination as similar to the first embodiment of the present invention. Further, since the workflow processing is implemented in the workflow navigation PC 24 independent of the ultrasound diagnosis apparatus 23, even an ultrasound diagnosis apparatus without a workflow processing feature may be applicable to the system according to an embodiment of the present invention, in which the workflow processing and supply information are realized in other components. If the system is placed within a hospital LAN, it may be flexible and easier where to place or move the ultrasound diagnosis apparatus 23, the workflow navigation PC 24, and the image display PC 25 as long as they are connectable to the LAN.

Even in the second embodiment of the present invention where the workflow processing program is in the workflow navigation PC24, it may be still possible to display the list of examination names, the icons corresponding to activities, and the like in the operator monitor 23a of the ultrasound diagnosis apparatus 23 via the hospital LAN or the communication lines 26 such as RS232C.

In the second embodiment of the present invention, it has been described that the workflow navigation PC24 is provided and stores the workflow processing program and the workflow data. However, the program and the data may be made to be stored in the image display PC 25. In this case, an embodiment of the present invention is implemented without the workflow navigation PC24 if the display regarding the workflow, such as a display of the list of examination names and a display of icons corresponding to activities, is made in the operator monitor 23a of the ultrasound diagnosis apparatus 23 via the hospital LAN or the communication lines 26 such as RS232C.

(Third Embodiment)

The first embodiment was an example showing that the production of image data and speech data for a patient were implemented in the main unit 1 of the ultrasound diagnosis apparatus. A third embodiment of the present invention is an example showing that the production of image data and speech data for a patient can be implemented in an independent PC.

Figure 6B:
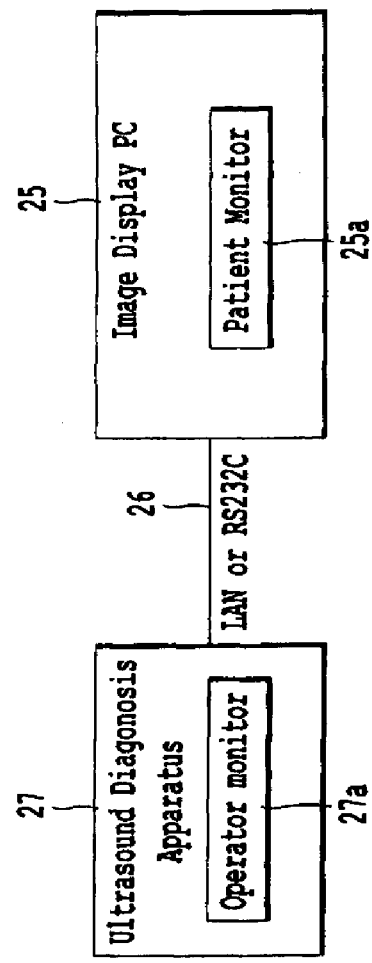
Figure 7:
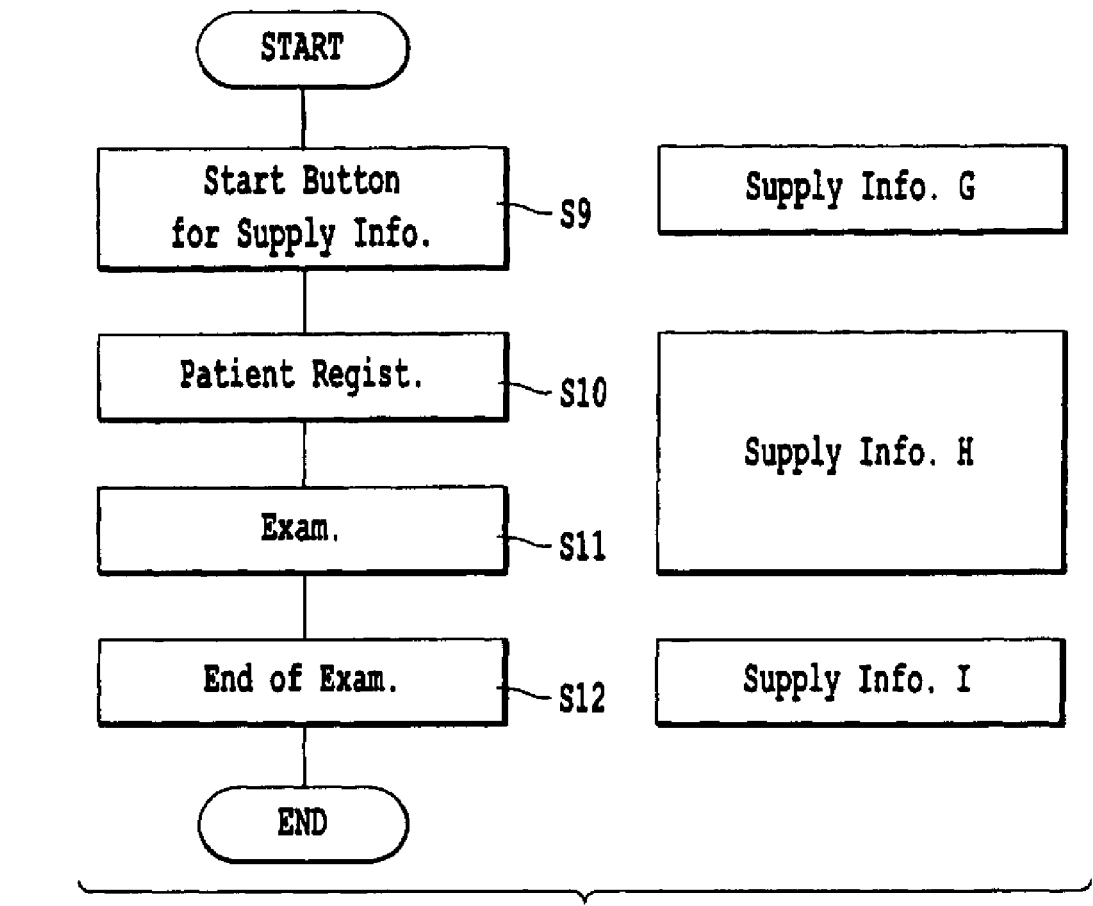
Figure 8:
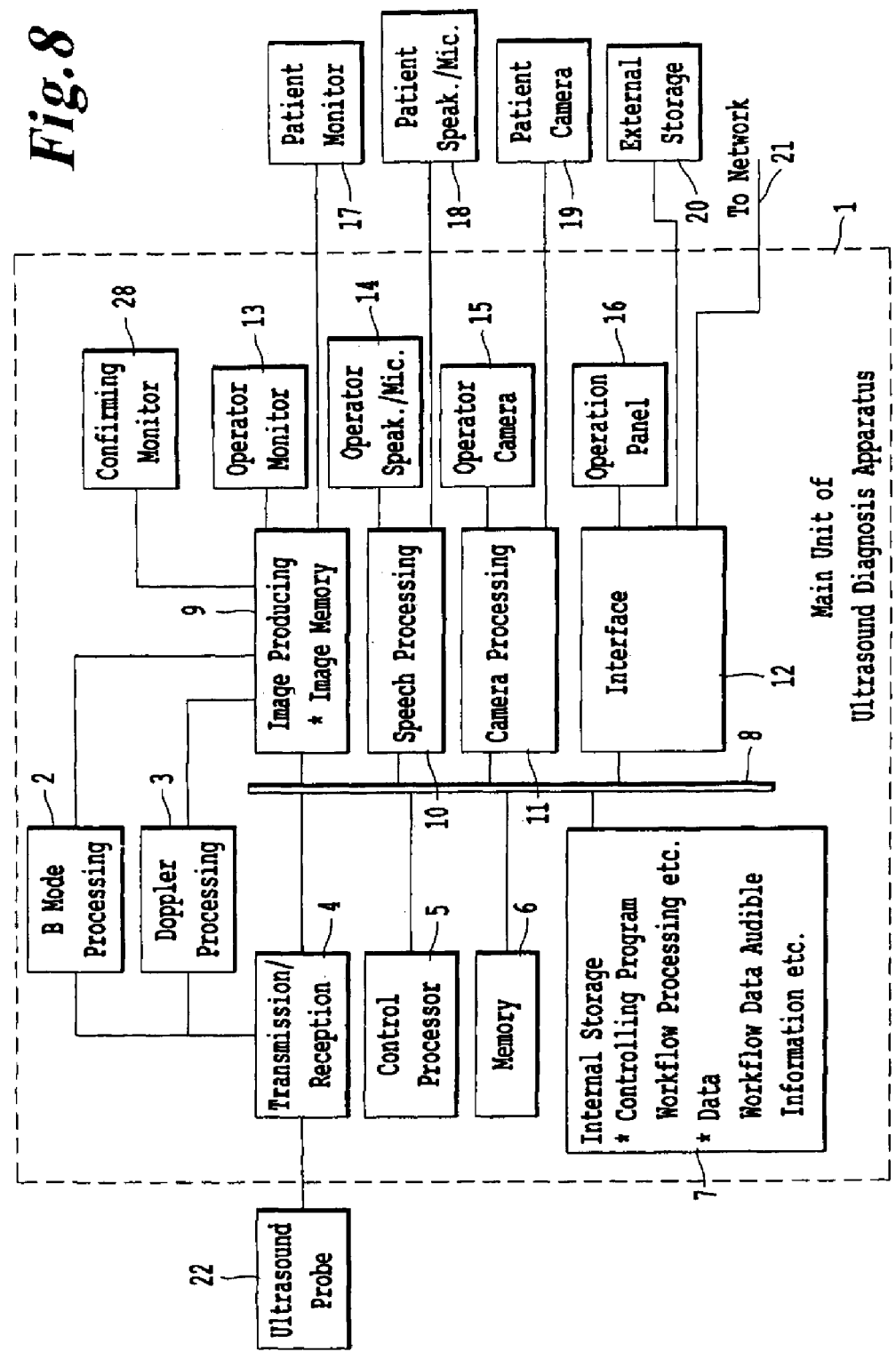
Figure 9:
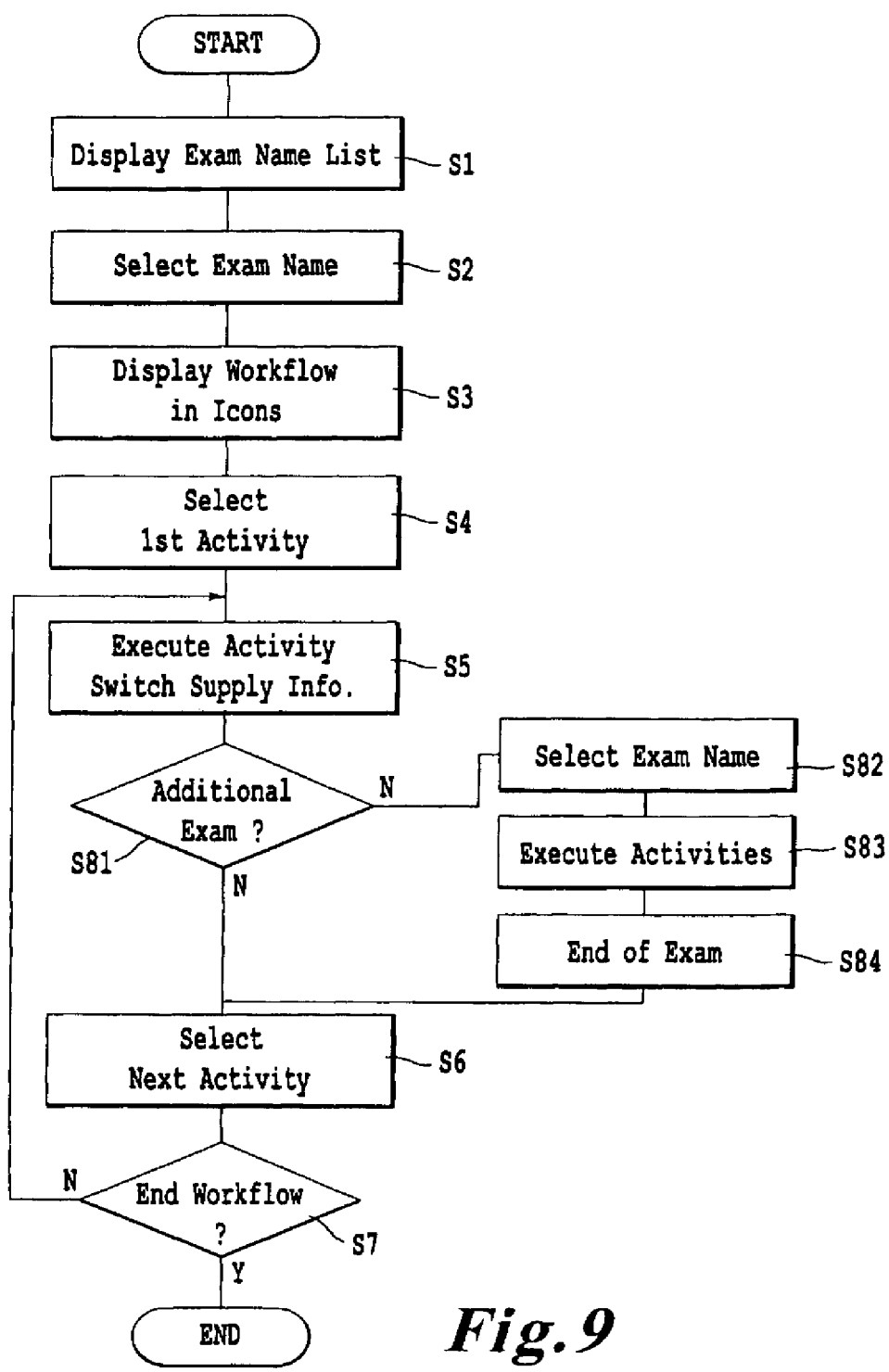
Figure 10:
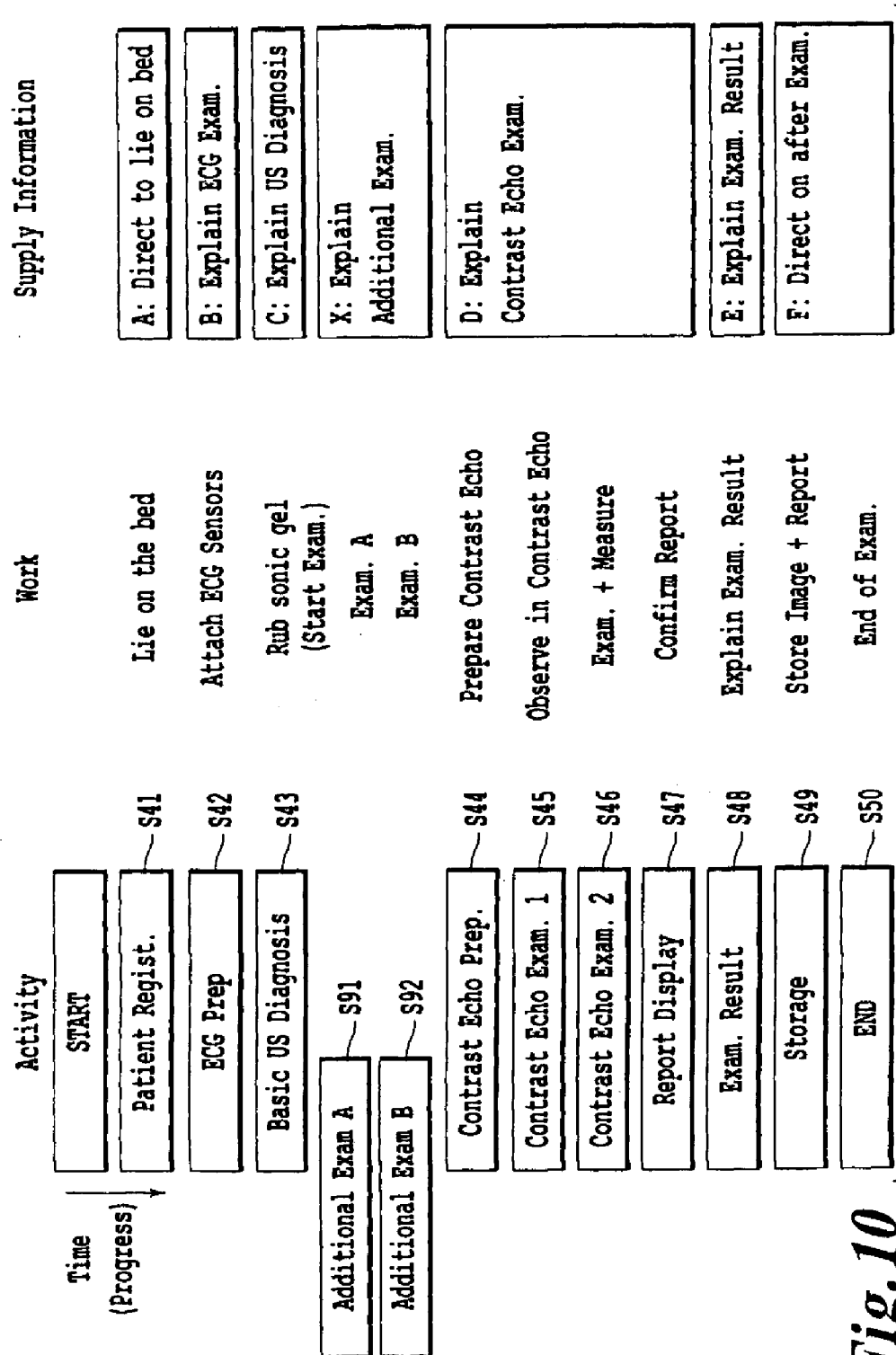

FIG. 6(b) is a block diagram showing an ultrasound diagnosis system according to the third embodiment of the present invention. In this embodiment, the same components as those described in the first embodiment are omitted.

The ultrasound diagnosis system in this embodiment comprises an ultrasound diagnosis apparatus 27 and the image display PC 25. These components are connected to each other in a mutually communicable form via the hospital LAN or the communication lines 26 such as RS232C. In addition, the ultrasound diagnosis apparatus 27 has an operator monitor 27a.

The workflow-processing program is executed in the ultrasound diagnosis apparatus 27 and performs operations in a similar manner as described in the first embodiment of the present invention. The workflow processing program controls the operator monitor 27a to display a list of examination names, icons corresponding to activities, and the like. The workflow-processing program also executes each activity sequentially and transmits control signals to the image display PC 25 via the communication lines 26. The control signals are produced in accordance with the contents defined in each activity. Responsive to the control signals, the image display PC 25 changes its operations to switch when to supply the supply information and to switch supply information at the appropriate times. For example, the supply information are images produced and audible information processed for the patient in the image display 25.

With the system described in the third embodiment of the present invention, similar effects obtained in the first embodiment are available. According to the third embodiment of the present invention, processing supply information is performed in the image display PC 25 so that the ultrasound diagnosis apparatus 27 may reduce its load.

As explained above, since image production and audible information processing for supply information are performed in the image display PC 25, as similar to the second embodiment of the present invention, an image display program, image data, and speech data for supply information, and the like may be stored in the image display PC 25.

Further, even in the above second embodiment of the present invention, as similar to the third embodiment, image production and audible information processing for supply information may be performed in the image display PC 25. In this case, even using a conventional ultrasound diagnosis apparatus, it may be possible that an operator may operate the conventional ultrasound diagnosis apparatus, following a workflow, and the operator may provide supply information in accordance with the workflow, as long as the operator changes the setting of the conventional apparatus manually by himself.

(Fourth Embodiment)

The first to the third embodiments of the present invention have been described such that the supply information to a patient is switched in conjunction with workflow processing. A fourth embodiment of the present invention, however, is an example that does not use workflow processing. In this embodiment, the supply information is switched in conjunction with input into the operation panel 16 of the ultrasound diagnosis apparatus.

In this embodiment, image production and audible information processing for the supply information may be performed in the ultrasound diagnosis apparatus or in the patient monitor 17. Also an image processing program and image data and speech data for supply information may be stored in the ultrasound diagnosis apparatus or in the patient monitor 17.

When they are implemented in the patient monitor 17, the ultrasound diagnosis apparatus outputs information to an external apparatus (e.g. the patient monitor 17) regarding operations in response to each operation in the ultrasound diagnosis apparatus. Such ultrasound diagnosis apparatus may be used in the fourth embodiment of the present invention without any more particular specifications for the apparatus. Responsive to the information regarding operations output from the ultrasound diagnosis apparatus, the patient monitor 17 may supply the patient with the supply information appropriate for each operation.

Figure 7:
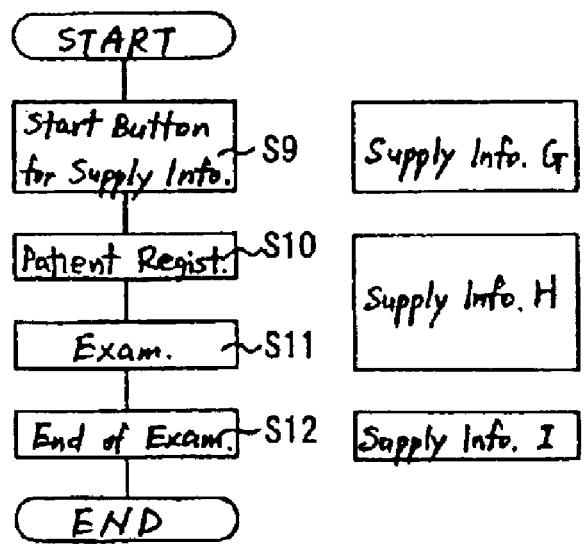
FIG. 7 is a flowchart showing relations between a flow in an ultrasound diagnosis apparatus and supply information according to a fourth embodiment of the present invention.

FIG. 7 is a flowchart showing relations between a flow in an ultrasound diagnosis apparatus and supply information according to the fourth embodiment of the present invention. The operator presses a button, on the operation panel 16, for starting supplying supply information (step S9). Responsive to the button, a controlling program for the ultrasound diagnosis apparatus controls the patient monitor 17 to display a direction-message, in characters, of 'please lie on the bed' with animation images (supply information G) which explains and shows how to lie on the bed for a coming examination. The patient lies on the bed, following this direction. For this step S9, a plurality kinds of supply information may be prepared and be selected by the operator.

Next, the operator operates the operation panel 16 and registers patient information such as a patient's name who is going to take an examination (step S10). Responsive to the operator's press of a registration completion button, the controlling program controls the patient monitor 17 and the patient speaker/microphone 18 to supply explanation of ultrasound diagnosis and relaxing information as supply information H. The explanation may include the purpose and contents of the ultrasound diagnosis, diseases which may be diagnosed by the ultrasound diagnosis, safety of the ultrasound diagnosis, and so on. After the explanation, there is also supplied information which makes the patient feel comfortable or relaxed mentally. While the supply information H is supplied to the patient, the operator operates the operation panel 16 and continues to perform actual examinations by switching diagnosis modes next by next if necessary (step S11).

When the all necessary actual examinations have been completed, the operator presses an examination completion button (step S12). The controlling program controls the patient monitor 17 and the patient speaker/microphone 18 to supply supply information I. For example, the supply information I may include directions to the patient on what to do and where to go after the examination has been completed, and a location map inside the hospital.

The fourth embodiment of the present invention has taken an example of switching supply information in conjunction with the completion input of patient information registration. In addition to the example, the supply information may also be switched in conjunction with the following conditions: changing of scanning modes in the ultrasound diagnosis apparatus; setting conditions, in ultrasound image production, such as a condition of ultrasound transmission/reception; execution/completion of data storage; directions of start/termination of acquiring data for producing ultrasound images; and operations of a measurement program for obtaining, from ultrasound images, measured values on such as a pulsarity index representing blood flow, a distance, and a beat of blood flow.

According to the fourth embodiment of the present invention, the supply information is switched in conjunction with operation switching of the ultrasound diagnosis apparatus and/or input operations of information. Therefore, it is possible to supply the patient with supply information, such as the following information at the appropriate time, respectively, during the examination: explanation of the (actual) examination; directions during the (actual) examination; information of the examination result; and information which makes the patient feel comfortable and relaxed mentally.

Such exemplary supply information makes it possible to reduce anxiety and/or boredom of the patient since, as explained above, the appropriate explanation is made to the patient regarding the contents of the (actual) examination. In addition, directions about the body positions can be made appropriately and plainly so that the examination progresses preferably. As a result, the examination efficiency is improved. Further, supply information can be switched in conjunction with input operations in operations of the ultrasound diagnosis apparatus. Therefore, the operator may be released from tangled operations. This results in improvement of the examination efficiency.

(Fifth Embodiment)

It has been described in the above embodiments of the present invention that an operator is equipped with only one monitor, that is, the operator monitor 13 (, 23*a*, or 27*a*). In this case, there is no way that the operator confirms that a patient is getting the appropriate information unless the operator directly looks into the patient monitor 17 (or 25*a*) himself.

Figure 8:
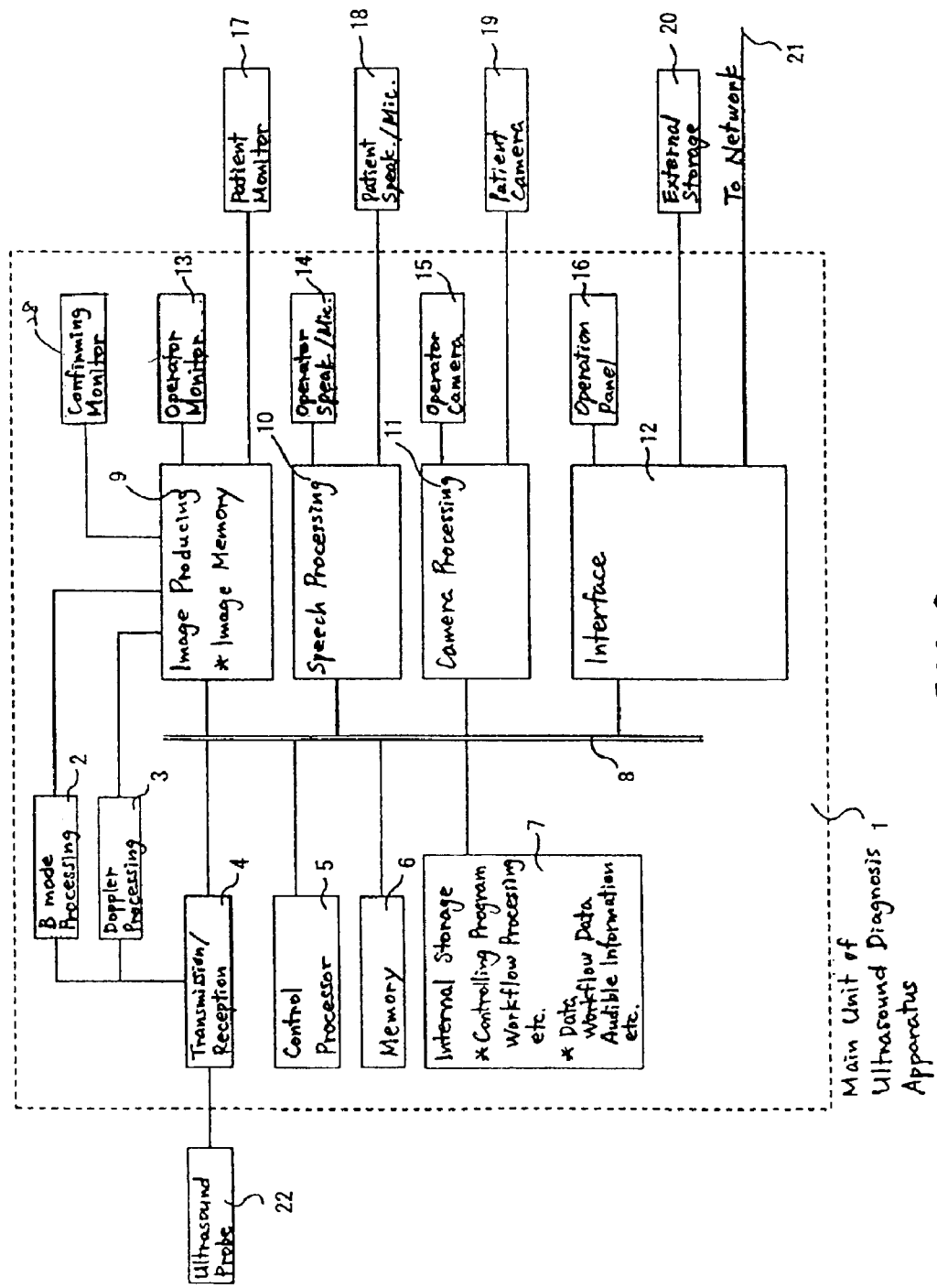
FIG. 8 is a block diagram showing an ultrasound diagnosis system according to a fifth embodiment of the present invention.

FIG. 8 is a block diagram showing an ultrasound diagnosis system according to a fifth embodiment of the present invention. In FIG. 8, the difference from the FIG. 1 is the presence of a confirming monitor 28, for confirming the contents displayed in the patient monitor 17, in the main unit 1 of the ultrasound diagnosis apparatus. In this embodiment, an explanation of the same components with the same reference numbers as those described in the first embodiment is omitted.

In this embodiment, the confirming monitor 28 can display the same contents as those which are displayed in the patient monitor 17. The image producing circuitry 9 is controlled that all the supply information to be displayed in the patient monitor 17 can be output to the confirming monitor 28 and be displayed therein.

Since the same information, that is, the supply information, is displayed in both the patient monitor 17 and the confirming monitor 28, the operator may confirm or check, when necessary, by looking at the confirming monitor 28 placed adjacent to the operator whether appropriate supply information is being displayed in the patient monitor 17 or which supply information is supplied to the patient. Accordingly, the operator does not have to be sensitive to the supply information being provided to the patient. This may lead to more concentration on the examination by the operator and result in improvement of the examination quality and efficiency.

When part of the supply information is supplied to the patient monitor 17 without through the image producing circuitry 9, such part of the supply information may also be supplied to the confirming monitor 28 without going through the image producing circuitry 9. As long as the same information is displayed in both the patient monitor 17 and the confirming monitor 28, the means for its achievement is not limited to those described in this embodiment.

Further, although this embodiment has been described to confirm what is displayed in the patient monitor 17 with the confirming monitor 28, it may be possible to obtain the same effect without such an extra monitor if the window of the operator monitor 13 is switched from what is usually displayed for the operator to the supply information, which is displayed in the patient monitor 17 as long as such window switching does not disturb the examination.

(Sixth Embodiment)

A sixth embodiment of the present invention will be described with reference to FIGS. 8 and 9. In an ultrasound diagnosis examination, it is not rare that other examinations are performed in addition to the ultrasound diagnosis, if necessary, during a current examination and such other examination is performed while the current examination is temporarily suspended.

Figure 9:
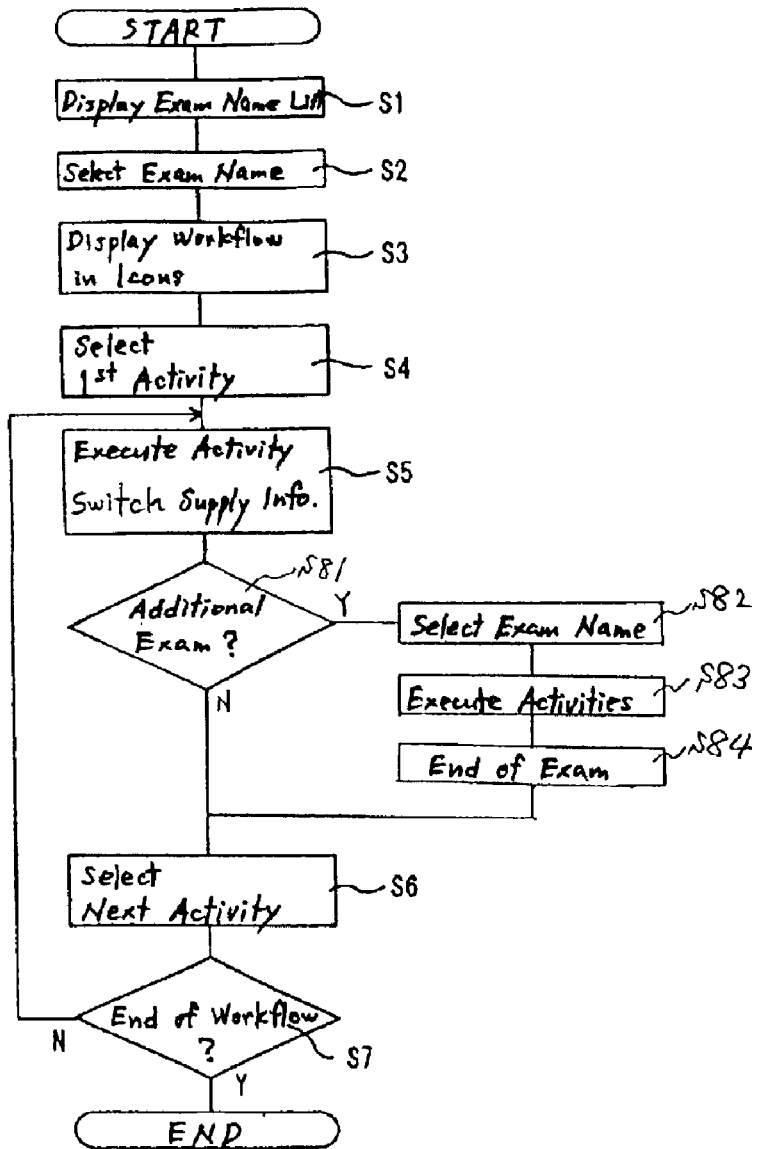
FIG. 9 is a flowchart showing a workflow-processing program according to a sixth embodiment of the present invention.

FIG. 9 is a flowchart showing a workflow-processing program according to the sixth embodiment of the present invention. In FIG. 9, the steps S1 to S7 are the same as described in FIG. 3 for the first embodiment of the present invention and so explanation of these steps is omitted in this sixth embodiment.

In step S5 of FIG. 9, a certain activity during a workflow of an examination is executed. Before the next activity is selected in step S6 in the workflow and the examination is progressed forward, the workflow is interrupted and temporarily suspended. An actual examination other than actual examinations scheduled in the workflow (hereinafter referred to as an additional examination) is performed if the operator decides that the additional examination should be performed at this stage before moving on to the next activity (step S81).

This additional examination is not limited to the above-mentioned case based on the operator's decision. The additional examination may be determined to be performed, for example, based on an advice or a direction by a doctor in another place. Further, it may be possible that additional examinations have been prepared in advance and are presented to be selected in the operator monitor as optional examinations only under a specific situation during the original workflow.

In any case, according to the decision for the additional examination, a name of the examination is selected by the operator or is automatically selected by the workflow because of the specific situation (step S82). Responsive to the selection, the original workflow processing is interrupted and temporarily suspended until completion of the selected additional examination. Activities according to a workflow corresponding to the name of the selected additional examination are executed (step S83). Execution of the activities for the selected additional examination follows the steps, in a similar manner to the first embodiment of the present invention, shown in the flowchart of FIG. 9.

When all of the activities for the selected additional examination have been completed, the selected additional examination becomes over and the workflow processing goes back to the original workflow (step S84). In the original workflow, an activity, which was to be selected just before the additional examination, is selected in step S6.

In accordance with the performance of the additional examination, an expected total time of the examination may become longer. Updated time information is estimated, upon selection of the additional examination, by correcting an expected total examination time and a time representing a progress of the examination.

Figure 10:
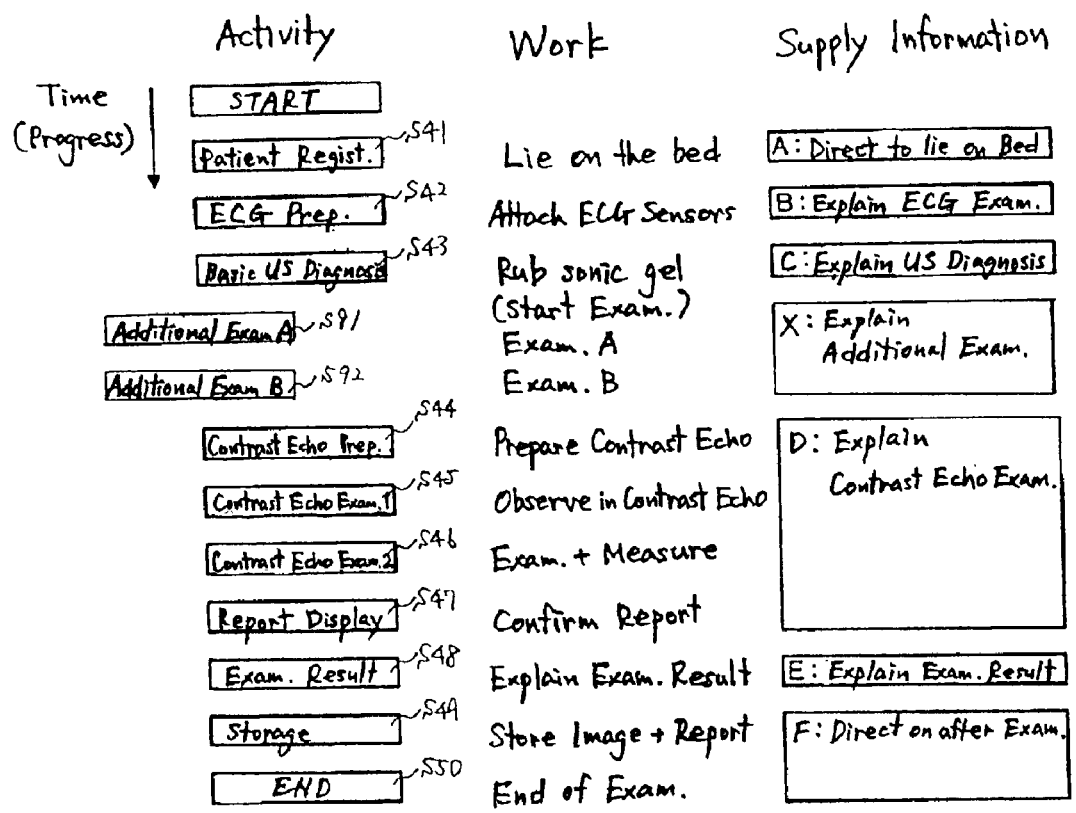
FIG. 10 is a schematic view showing relations between examinations and supply information following a workflow according to the sixth embodiment of the present invention.

Next, FIG. 10 is a schematic view showing relations between examinations and supply information following a workflow according to the sixth embodiment of the present invention. In FIG. 10, steps S41 to S50 are the same as described in the FIG. 5 for the first embodiment of the present invention and so explanation of these steps is omitted in the sixth embodiment.

Each activity is executed in accordance with the workflow-processing program. For example, if the operator decides that an additional examination should be performed when an activity "basic ultrasound diagnosis" has been executed in step S43 (corresponding to 'yes' in step S81 in FIG. 9), the workflow processing does not immediately go to the next activity "contrast echo preparation" (step 44). The additional examination is cut into or inserted in the workflow processing.

When there are two additional examinations A and B, responsive to the operator's selection of an additional examination A, an activity "additional examination A" (step S91) is executed. The workflow-processing program controls the operator monitor 13 to display a message to urge preparation for the additional examination A. Following the message, the operator prepares for the additional examination A. The operator starts to perform the additional examination A when the preparation has been completed.

For the patient, responsive to the selection of the additional examination A, the workflow processing program controls the patient monitor 17 and the patient speaker/microphone 18 to supply explanation of the additional examination A and relaxing information as supply information X. After the explanation of the additional examination A, there are provided a landscape image which makes a patient feel comfortable or relaxed mentally, an image of a well-known picture, music, and/or the like.

After the additional examination A has been completed, the operator may select the following additional examination B. Upon this selection, an activity "additional examination B" (step S92) is executed in a similar manner to the additional examination A.

When both of the additional examinations A and B have been completed, the activity "contrast echo preparation" (step S44) which was to be selected just before the additional examination A, is selected (corresponding to step S6 in FIG.

9) and executed. Afterwards, the activities S45 to S50 are executed in a similar manner to the first embodiment of the present invention.

As explained above, even if additional examinations are cut into or inserted in a workflow corresponding to an original examination, supply information corresponding to the additional examinations is supplied to the patient. Therefore, the patient may correctly figure out a current status of the examination such as the followings: how the examination is developing; what the purpose of the examination is; and how much a total time of the examination is extended by additional examinations. Further, during the examination except for the time of explaining the examination, there is supplied supply information which makes a patient feel mentally comfortable. Therefore, the patient may take examinations without much anxiety.

The operator is provided flexibility in a workflow processing even when an additional examination is required. This can avoid losing efficiency of examinations.

Compared to an MRI examination, an examination by an ultrasound diagnosis apparatus often requires additional examinations flexibly cut into an original examination as shown in the sixth embodiment of the present invention. Accordingly, the sixth embodiment may be particularly more effective for diagnoses with an ultrasound diagnosis apparatus.

The present invention is not limited to the above-explained embodiments, but may be modified in various manners within a scope of the present invention. For example, although an ultrasound diagnosis apparatus has been taken as an example throughout the above-explained embodiments, other medical diagnosis apparatus such as a CT apparatus, an MRI apparatus, and an X-ray diagnosis apparatus may be applicable to the present invention.

Embodiments of the present invention are not limited to the circuitry structure and/or the hardware devices described in the above embodiments, but may be implemented to execute software in a conventional PC (personal computer) which enables processing similar to the circuitries or devices. Such software may also be executed, for example, in a medical diagnosis apparatus or in a monitor (display) placed adjacent to a patient by being installed such software therein.

As an example of the above, a hardware device wherein the software is executed, may have a random access memory (RAM), which can receive and store program modules and applications as computer readable instructions in a temporary and/or non-volatile state. The hardware device may further have a hard disk drive for reading from and writing to a hard disk, a magnetic disk drive for reading and writing to a removable magnetic disk, and an optical disk drive for reading and writing to and from a removable optical disk (such as a CD, CDR, CD-RW, DVD, or other optical device). Those skilled in the art will appreciate that such memory, drives, and their respective media are examples of computer-readable medium for storing computer readable instructions which when executed may implement an embodiment of the present invention.

Further, supply information may be a TV program in addition to or in conjunction with the example supply information described above. A patient usually enjoys watching TV and, only when necessary, the TV is interrupted by display of examination explanation, directions, and the like.

Furthermore, supply information may be stored in a server (a storage apparatus) independent of a medical diagnosis apparatus and any other monitors or PCs. Desired supply information may be retrieved from the server via a communication network when it is needed. In this case, it may not be so difficult to update supply information stored in the server. Instead of landscape images or so, it may be possible to supply a patient with daily news updated every day.

With supply information stored in such an independent server, it may be possible to supply a patient with more kinds of supply information, and also to reduce the load in the hardware of the system components since the supply information does not need to be stored in any of a medical diagnosis apparatus, a workflow navigation PC, and an image display PC (patient monitor).

Still further, the audible information such as directions or information made by speech may be based on an actual utterance of an operator, prerecorded speech, or a speech synthesizer.

Through the embodiments of the present invention, there has been described a medical diagnosis system equipped with an operator camera and a patient camera. These cameras, however, may be more useful in an X-ray diagnosis system, a CT diagnosis system, and an MRI diagnosis system than in an ultrasound diagnosis system in which an operator and a patient tend to be situated adjacent to each other.

What is claimed is:

1. A medical diagnosis system wherein a medical image is produced in a medical diagnosis apparatus, the system comprising:

first storing means for storing an examination procedure for the medical diagnosis apparatus;

second storing means for storing first supply information to be supplied to a patient of the medical diagnosis apparatus, the first supply information including information used for a purpose of at least one of entertainment, relaxation, comfort, and explanation of the examination procedure;

first supply means for supplying the patient with the first supply information stored in the second storing means, the first supply means including a patient monitor confirmed to visibly display at least part of the first supply information;

second supply means for supplying an operator of the medical diagnosis apparatus with second supply information which is different from the first supply information, the second supply means including an operator monitor configured to display the medical image; and controlling means for controlling that the first supply information is supplied by the first supply means in accordance with the examination procedure stored in the first storing means.

2. The medical diagnosis system according to claim 1, further comprising second controlling means for controlling the medical diagnosis apparatus in accordance with the examination procedure stored in the first storing means.

3. The medical diagnosis system according to claim 1, wherein the first storing means, the second storing means, and the controlling means are provided in the medical diagnosis apparatus.

4. The medical diagnosis system according to claim 1, wherein the first supply information includes information related to an examination and information not-directly related to the examination.

5. The medical diagnosis system according to claim 1, wherein the first storing means and the controlling means are provided in a first computer; the medical diagnosis apparatus is controlled in accordance with a first control signal from the controlling means; and the first supply means is provided in a second computer, the first supply means supplying the first supply information in accordance with a second control signal from the controlling means.

6. The medical diagnosis system according to claim 1, wherein the first storing means and the controlling means are provided in the medical diagnosis apparatus and the first supply means is provided in a computer, the first supply means supplying the first supply information in accordance with a control signal from the controlling means.

7. The medical diagnosis system according to claim 1, wherein the controlling means controls the supply means to supply time information related to a medical examination as part of the supply information.

8. The medical diagnosis system according to claim 1, further comprising a camera for taking a second image, and wherein the controlling means controls the supply means to supply the second image taken by the camera as part of the supply information.

9. The medical diagnosis system according to claim 1, wherein the controlling means controls the supply means to supply the supply information along with audible information.

10. The medical diagnosis system according to claim 1, further comprising: a microphone, provided near the medical diagnosis apparatus, for collecting audible information; and a speaker, included in the supply means, for supplying the audible information collected by the microphone.

11. The medical diagnosis system according to claim 1, wherein the second storing means is provided independent of the medical diagnosis apparatus.

12. The medical diagnosis system according to claim 1, wherein the second supply means is further configured to display the visible part of the supply information supplied in the supply means.

13. The medical diagnosis system according to claim 1, further comprising a second operator monitor provided near the medical diagnosis apparatus, configured to visibly display part of the first supply information supplied by the first supply means.

14. The medical diagnosis system according to claim 1, wherein the supply information includes at least one of an instruction to the patient and an explanation to the patient of an examination by the medical diagnosis apparatus.

15. A medical diagnosis system wherein a medical image is produced in a medical diagnosis apparatus, the system comprising:

first storing means for storing a plurality of workflows each of which includes a corresponding examination procedure for the medical diagnosis apparatus;

second storing means for storing first supply information to be supplied to a patient of the medical diagnosis apparatus, the first supply information including information used for a purpose of at least one of entertainment, relaxation, comfort, and explanation of the examination procedure;

first supply means for supplying the patient with first supply information stored in the second storing means, the first supply means including a patient monitor configured to visibly display at least part of the first supply information;

second supply means for supplying an operator of the medical diagnosis apparatus with second supply information which is different from the first supply information, the second supply means including an operator monitor configured to display the medical image;

selecting means for selecting a workflow from the workflows stored in the first storing means; and controlling means for controlling that first supply information is supplied by the first supply means in accordance with the workflow selected by the selecting means, wherein the one of the first supply information supplied by the first supply means is switched from one piece of first supply information to another in accordance with a progress of the selected workflow and the second supply information supplied by the second supply means is switched from one piece of second supply information to another in accordance with a progress of the selected workflow.

16. A medical diagnosis system wherein a medical image is produced in a medical diagnosis apparatus, the system comprising:

input means for input operations;

storing means for storing first supply information to be supplied to a patient of the medical diagnosis apparatus, the first supply information including information used for a purpose of at least one of entertainment, relaxation, comfort, and explanation of an examination procedure of the medical diagnosis apparatus;

first supply means for supplying the patient with the first supply information stored in the storing means, the first supply means including a patient monitor configured to visibly display at least part of the first supply information;

second supply means for supplying an operator of the medical diagnosis apparatus with second supply information which is different from the first supply information, the second supply means including an operator monitor configured to display the medical image; and controlling means for controlling that the first supply information is supplied by the first supply means in accordance with the input operations by the input means.

17. A medical diagnosis system wherein a medical image is produced in a medical diagnosis apparatus, the system comprising:

input means for inputting information regarding a patient;

storing means for storing first supply information to be supplied to a patient of the medical diagnosis apparatus, the first supply information including information used for a purpose of at least one of entertainment, relaxation, comfort, and explanation of an examination procedure of the medical diagnosis apparatus;

first supply means for supplying the patient with the first supply information stored in the storing means on the basis of the information input by the input means, the first supply means including a patient monitor configured to visibly display at least part of the first supply information; and second supply means for supplying an operator of the medical diagnosis apparatus with second supply information which is different from the first supply information, the second supply means including an operator monitor configured to display the medical image.

18. The medical diagnosis system according to claim 17, wherein the information input by the input means includes information regarding at least one of sex, age, and medical condition of a patient.

19. An ultrasound diagnosis apparatus for a use in a medical diagnosis system, the ultrasound diagnosis apparatus comprising:
   image producing means for producing an ultrasound image;
   display means for displaying the ultrasound image produced by the image producing means;
   first storing means for storing an examination procedure related to the ultrasound diagnosis apparatus;
   second storing means for storing supply information to be supplied to a patient of the ultrasound diagnosis apparatus, the supply information including information used for a purpose of at least one of entertainment, relaxation, comfort, and explanation of the examination procedure;
   an independent apparatus provided for the patient and including a patient monitor configured to visibly display at least part of the supply information; and
   controlling means for controlling that the supply information is output to the independent apparatus so as to be supplied to the independent apparatus in accordance with the examination procedure stored in the storing means.

20. A medical diagnosis apparatus producing a medical image, the apparatus comprising:
   a memory which stores an examination procedure related to the medical diagnosis apparatus;
   a second memory which stores supply information to be supplied to a patient of the ultrasound diagnosis apparatus, the supply information including information used for a purpose of at least one of entertainment, relaxation, comfort, and explanation of the examination procedure;
   an independent apparatus provided for the patient and including a patient monitor configured to visibly display at least part of the supply information;
   a processor which is operative to output the supply information to the independent apparatus so that the supply information is supplied to the independent apparatus in accordance with the examination procedure stored in the memory; and
   a display provided for an operator of the medical diagnosis apparatus, for displaying the medical image.

21. An information apparatus for a use in a medical diagnosis system including a medical diagnosis apparatus which produces and displays a medical image, the information apparatus comprising:
   first storing means for storing an examination procedure of the medical diagnosis apparatus;
   second storing means for storing supply information to be supplied to a patient of the medical diagnosis apparatus, the supply information including information used for a purpose of at least one of entertainment, relaxation, comfort, and explanation of the examination procedure;
   supply means for supplying the patient with the supply information stored in the second storing means, the supply means including a patient monitor configured to visibly display at least part of the supply information; and
   controlling means for controlling that the supply information is supplied by the supply means in accordance with the examination procedure stored in the first storing means.

22. An information apparatus for a use in a medical diagnosis system including a medical diagnosis apparatus which produces and displays a medical image, the information apparatus comprising:
   receiving means for receiving an information signal output from the medical diagnosis apparatus;
   storing means for storing supply information to be supplied to a patient of the medical diagnosis apparatus, the supply information including information used for a purpose of at least one of entertainment, relaxation, comfort, and explanation of an examination procedure of the medical diagnosis apparatus;
   supply means for supplying the patient with the supply information stored in the storing means, the supply means including a patient monitor configured to visibly display at least part of the supply information; and
   controlling means for controlling that the supply information is supplied by the supply means in accordance with the information signal received by the receiving means.

23. A method of controlling a medical diagnosis system wherein a medical image is produced in a medical diagnosis apparatus and displayed in an operator monitor, the method comprising steps of:
   selecting an examination procedure;
   operating the medical diagnosis apparatus in accordance with the selected examination procedure;
   supplying to a patient monitor supply information, including information used for a purpose of at least one of entertainment, relaxation, comfort, and explanation of the examination procedure, for viewing by the patient; and
   switching one piece of supply information to another piece of supply information in accordance with the selected examination procedure.

24. A method of controlling a medical diagnosis system wherein a medical image is produced in a medical diagnosis apparatus and displayed in an operator monitor, the method comprising steps of:
   selecting a plurality of examination procedures;
   operating the medical diagnosis apparatus in accordance with the selected examination procedures; and
   supplying a patient with supply information corresponding to each kind of the selected examination procedures through a patient monitor, the supply information including information used for a purpose of at least one of entertainment, relaxation, comfort, and explanation of the examination procedure.

25. A method of controlling a medical diagnosis system wherein a medical image is produced in a medical diagnosis apparatus, the method comprising steps of:
   selecting one examination from a plurality of examinations;
   displaying a plurality of examination procedures corresponding to the one selected examination;
   selecting each examination procedure from the displayed examination procedures;
   supplying a patient with supply information corresponding to the each selected examination procedure through a patient monitor, the supply information including information used for a purpose of at least one of entertainment, relaxation, comfort, and explanation of the examination procedure, supplying an operator of the medical diagnosis apparatus with operator information which is different from the supply information through an operator monitor configured to display the medical image; and switching the operator information displayed by the operator monitor from one piece of operator information to another in accordance with the each selected examination procedure.

26. A computer-readable medium on which is stored a program module for supplying a patient with information in a medical diagnosis system wherein a medical image is produced, the program module comprising instructions, which when executed perform steps comprising:

selecting one examination from a plurality of examinations;

displaying a plurality of examination procedures corresponding to the one selected examination;

selecting each examination procedure from the displayed examination procedures;

supplying the patient with supply information corresponding to the each selected examination procedure through a patient monitor, the supply information including information used for a purpose of at least one of entertainment, relaxation, comfort, and explanation of the examination procedure, supplying an operator of the medical diagnosis apparatus with operator information which is different from the supply information through an operator monitor configured to display the medical image; and switching the operator information displayed by the operator monitor from one piece of operator information to another in accordance with the each selected examination procedure.

* * * * *

UNITED STATES PATENT AND TRADEMARK OFFICE
CERTIFICATE OF CORRECTION

| | |
|---|---|
| PATENT NO. | : 6,872,179 B2 |
| APPLICATION NO. | : 10/191476 |
| DATED | : March 29, 2005 |
| INVENTOR(S) | : Naohisa Kamiyama et al. |

It is certified that error appears in the above-identified patent and that said Letters Patent is hereby corrected as shown below:

The title page should be deleted and substitute therefor the attached title page.

Replace the attached ten sheets of formal drawings including all figures 1 through 10 for the informal drawings printed in the patent, covering from pages 2 to 11.

Signed and Sealed this

Twenty-fourth Day of March, 2009

JOHN DOLL
*Acting Director of the United States Patent and Trademark Office*

United States Patent
Kamiyama et al.

(10) Patent No.: US 6,872,179 B2
(45) Date of Patent: Mar. 29, 2005

(54) MEDICAL DIAGNOSIS SYSTEM HAVING A MEDICAL DIAGNOSIS APPARATUS AND A DISPLAY TO BE OBSERVED BY A PATIENT

(75) Inventors: Naohisa Kamiyama, Tochigi-ken (JP); Akihiro Sano, Tochigi-ken (JP); Yoichi Ogasawara, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 138 days.

(21) Appl. No.: 10/191,476

(22) Filed: Jul. 10, 2002

(65) Prior Publication Data

US 2003/0026464 A1 Feb. 6, 2003

(30) Foreign Application Priority Data

Jul. 10, 2001 (JP) .......................... 2001-208720

(51) Int. Cl.[7] .................................................. A61B 8/00
(52) U.S. Cl. ............................... 600/437; 600/443
(58) Field of Search ................................ 600/407–472; 73/625, 626; 367/7, 11, 130, 138; 128/916; 382/128; 700/231, 237; 705/2–3, 52, 56

(56) References Cited

U.S. PATENT DOCUMENTS

| 5,412,419 A | 5/1995 | Ziarati | |
|---|---|---|---|
| 6,063,030 A | * 5/2000 | Vara et al. | 600/437 |
| 6,117,079 A | * 9/2000 | Brackett et al. | 600/437 |
| 6,526,163 B1 | * 2/2003 | Halmann et al. | 382/128 |
| 6,595,924 B2 | * 7/2003 | Kawae et al. | 600/437 |

FOREIGN PATENT DOCUMENTS

| JP | 1-249044 | 10/1989 |
|---|---|---|
| JP | 3141419 | 12/2000 |
| JP | 2001-137237 | 5/2001 |

* cited by examiner

*Primary Examiner*—Ali Imam
(74) *Attorney, Agent, or Firm*—Oblon, Spivak, McClelland, Maier & Neustadt, P.C.

(57) ABSTRACT

A medical diagnosis system wherein a medical image is produced in a medical diagnosis apparatus, comprises a first storage device which stores an examination procedure for the medical diagnosis apparatus, a second storage device which stores supply information, a supply device which supplies the supply information stored in the second storage device, and a control processor which controls that the supply information is supplied in the supply device in accordance with the examination procedure stored in the first storage device.

26 Claims, 10 Drawing Sheets

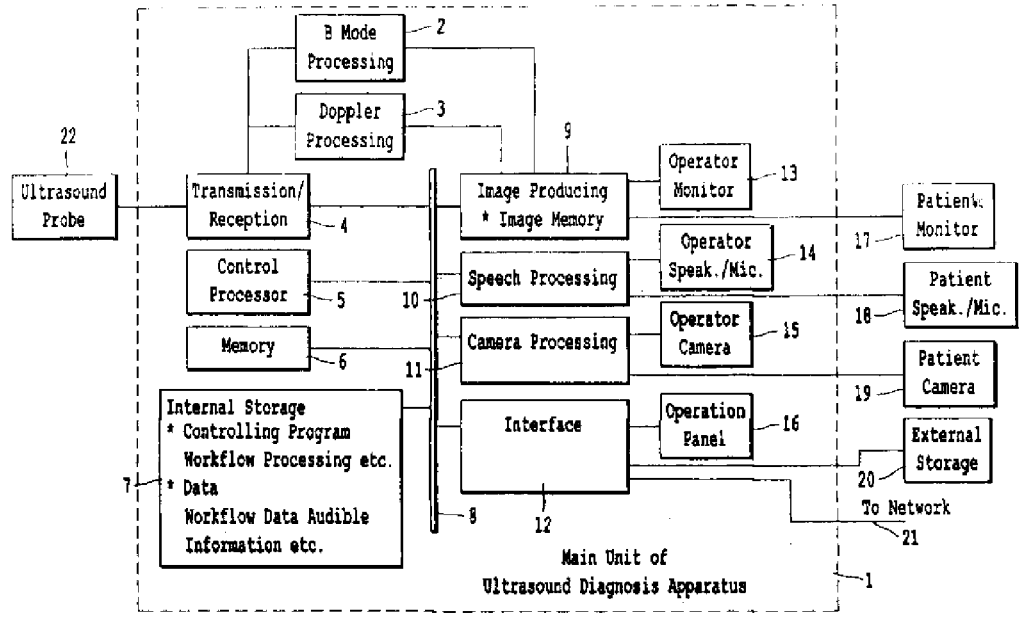

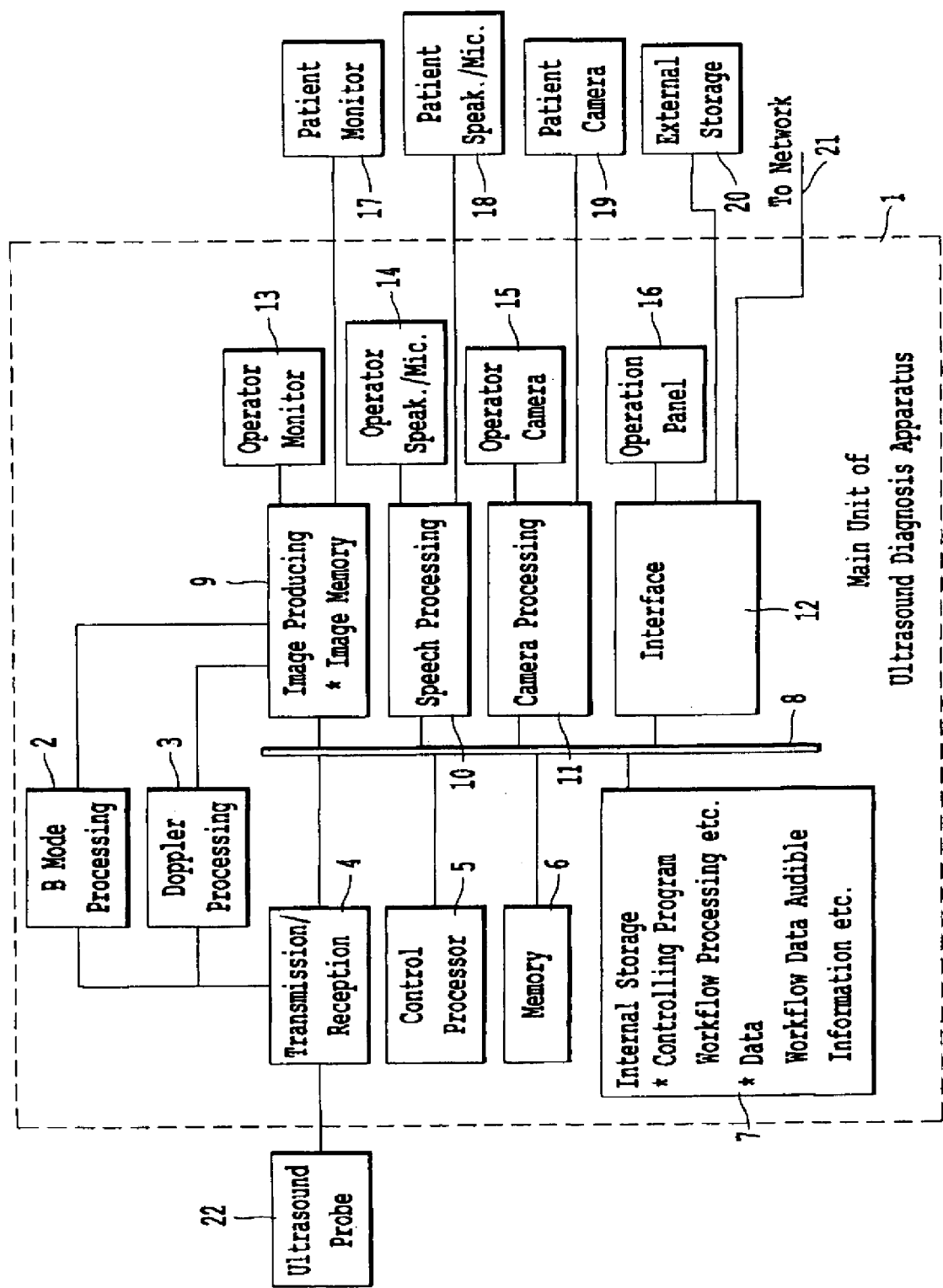

| Exam. Name | Workflow Data | Contents (Actual Exam.) | Supply Information |
|---|---|---|---|
| Myocardial Infarction Examination | Workflow Data A | ·Basic US Diagnosis<br>·Heart Contrast Echo<br>·Reporting | ·US Exam. Explanation<br>·Contrast Echo Exam. Explanation |
| Hepatic Cancer Examination | Workflow Data B | ·Basic US Diagnosis<br>·Liver Contrast Echo<br>·Reporting | ·US Exam. Explanation<br>·Contrast Echo Exam. Explanation |
| Fetal Growth Examination | Workflow Data C | ·Basic US Diagnosis<br>·Fetus Measurement<br>·Reporting | ·US Exam. Explanation<br>·Fetal Growth Explanation |

*Fig.4*